US007432353B2

(12) United States Patent
Lee et al.

(10) Patent No.: US 7,432,353 B2
(45) Date of Patent: Oct. 7, 2008

(54) FLUORESCENT INDICATOR PROTEINS

(75) Inventors: Seung-Goo Lee, Daejeon (KR); Jae-Jun Song, Daejeon (KR); Jae-Seok Ha, Daejeon (KR); Young-Mi Lee, Pohang-si (KR); Jeong-Min Lee, Daegu-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 11/492,618

(22) Filed: Jul. 25, 2006

(65) Prior Publication Data
US 2007/0020714 A1    Jan. 25, 2007

(30) Foreign Application Priority Data
Jul. 25, 2005    (KR) .................. 10-2005-0067353

(51) Int. Cl.
| C07H 21/04 | (2006.01) |
| C07K 14/435 | (2006.01) |
| C12P 21/02 | (2006.01) |
| C12P 21/06 | (2006.01) |
| C12P 19/02 | (2006.01) |
| C12Q 1/37 | (2006.01) |
| C12Q 1/54 | (2006.01) |

(52) U.S. Cl. .................. 530/350; 536/23.7; 435/14; 435/69.1; 435/69.7

(58) Field of Classification Search .................. None
See application file for complete search history.

(56) References Cited

U.S. PATENT DOCUMENTS 6,911,199 B2 *    6/2005    Vigne et al. .................. 424/93.2

FOREIGN PATENT DOCUMENTS

| WO | WO-98/40477 A1 | 9/1998 |
| WO | WO-03/025220 A2 | 3/2003 |
| WO | WO-2005/036178 A1 | 4/2005 |

OTHER PUBLICATIONS

GenBank Accession No. NP_626482.*
GenBank Accession No. CAB65651.*
Chauduri, Bernali Neel, et al., Structure of -allose binding protein from *Escherichia coli* bound to -allose at 1.8 Å resolution, J. Mol. Biol., Mar. 12, 1999, pp. 1519-1531, vol. 286, No. 5.
De Lorimier, Robert M., et al., Construction of a fluorescent biosensor family, Protein Science, Nov. 2002, pp. 2655-2675, vol. 11, No. 11.
Deuschle, Karen, et al., Construction and optimization of a family of genetically encoded metabolite sensors by semirational protein engineering, Protein Science, Sep. 2005, pp. 2304-2314, vol. 14, No. 9.
Dong, Min, et al., Using fluorescent sensors to detect botulinum neurotoxin activity in vitro and in living cells, Proc. Natl. Acad. Sci. USA, Oct. 12, 2004, pp. 14701-14706, vol. 101, No. 41.

Fehr, Marcus, et al., Visualization of maltose uptake in living yeast cells by fluorescent nanosensors, Proc. Natl. Acad. Sci. USA, Jul. 23, 2002, pp. 9846-9851, vol. 99, No. 15.
Fehr, Marcus, et al., In Vivo Imaging of the Dynamics of Glucose Uptake in the Cytosol of COS-7 Cells by Fluorescent Nanosensors, J. Biol. Chem., May 23, 2003, pp. 19127-19133, vol. 278, No. 21.
Fehr, Marcus, et al., Minimally invasive dynamic imaging of ions and metabolites in living cells, Curr. Opin. Plant Biol., Jun. 2004, pp. 345-351, vol. 7, No. 3.
Fukada, Harumi, et al., Thermodynamics of the binding of L-arabinose and of D-galactose to the L-arabinose-binding protein of *Escherichia coli*, J. Biol. Chem., Nov. 10, 1983, pp. 13193-13198, vol. 258, No. 21.
Guntas, Gurkan, et al., Creation of an Allosteric Enzyme by Domain Insertion, J. Mol. Biol., Feb. 6, 2004, pp. 263-273, vol. 336, No. 1.
Guntas, Gurkan, et al., Directed evolution of protein switches and their application to the creation of ligand-binding proteins, Proc. Natl. Acad. Sci. USA, Aug. 9, 2005, pp. 11224-11229, vol. 102, No. 32.
Kim, Changhoon, et al., The D-allose operon of *Escherichia coli* K-12, J. Bacteriol., Dec. 1997, pp. 7631-7637, vol. 179, No. 24.
Lager, Ida, et al., Development of a fluorescent nanosensor for ribose , FEBS Letters, Oct. 9, 2003, pp. 85-89, vol. 553, No. 1-2.
Looger, Loren L., et al., Computational design of receptor and sensor proteins with novel functions, Nature, May 8, 2003, pp. 185-190, vol. 423, No. 6936.
Magnusson, Ulrika, et al., Hinge-bending Motion of D-Allose-binding Protein from *Escherichia coli*, J. Biol. Chem., Apr. 19, 2002, pp. 14077-14084, vol. 277, No. 16.
Marvin, J.S., et al., The rational design of allosteric interactions in a monomeric protein and its applications to the construction of . . . , Proc. Natl. Acad. Sci. USA, Apr. 1997, pp. 4366-4371, vol. 94.
Miyawaki, Atsushi, et al., Fluorescent indicators for Ca2+based on green fluorescent proteins and calmodulin, Nature, Aug. 28, 1997, pp. 882-887, vol. 388.
Mochizuki, Naoki, et al., Spatio-temporal images of growth-factor-induced activation of Ras and Rap1, Nature, Jun. 28, 2001, pp. 1065-1068, vol. 411, No. 6841.

(Continued)

*Primary Examiner*—Anish Gupta
*Assistant Examiner*—Julie Ha
(74) *Attorney, Agent, or Firm*—David Bradin; Intellectual Property/Technology Law

(57) ABSTRACT

A protein biosensor having increased signal intensity to sugar concentration and the use thereof. A fluorescent indicator protein is described, in which fluorescent proteins of different emission ranges are fused to both ends of a binding protein undergoing a conformational change due to binding of sugars, such that a change in the concentration of various sugars involved in intracellular metabolism, e.g., maltose, can be detected by measuring a change in emission intensities, caused by FRET (fluorescence resonance energy transfer). A method for detecting a change in the concentration of sugars using such fluorescent indicator protein is also described. The fluorescent indicator protein has excellent signal intensity enabling precision measurement of intracellular concentration of various sugars. In one implementation, high signal intensity fluorescent indicator proteins can be prepared from proteins otherwise used as biosensors, to enable them to be more widely useful.

7 Claims, 13 Drawing Sheets

OTHER PUBLICATIONS

Nagai, Takeharu, et al., Circularly permuted green fluorescent proteins engineered to sense Ca2+, Proc. Natl. Acad. Sci. USA, Mar. 13, 2001, pp. 3197-3202, vol. 98, No. 6.

Nagai, Takeharu, et al., Expanded dynamic range of fluorescent indicators for Ca2+ by circularly permuted yellow fluorescent proteins, Proc. Natl. Acad. Sci. USA, Jul. 20, 2004, pp. 10554-10559, vol. 101, No. 29.

Okumoto, Sakiko, et al., Detection of glutamate release from neurons by genetically encoded surface-displayed FRET nanosensors, Proc. Natl. Acad. Sci. USA, Jun. 14, 2005, pp. 8740-8745, vol. 102, No. 24.

Patterson, George H., et al., Förster Distances between Green Fluorescent Protein Pairs, Anal. Biochem., Sep. 10, 2000, pp. 438-440, vol. 284, No. 2.

Patterson, George, et al., Fluorescent protein spectra, J. Cell Sci., Mar. 1, 2001, pp. 837-838, vol. 114, No. 5.

Sohn, J.-H., et al., Process Development for the Production of Recombinant Hirudin in *Saccharomyces cerevisiae*: from Upstream to Downstream, Process Biochemistry, 1995, pp. 653-660, vol. 30, No. 7.

Spurlino, J.C., et al., The 2.3-A resolution structure of the maltose- or maltodextrin-binding protein, a primary receptor of bacterial active . . . , J. Biol. Chem., Mar. 15, 1991, pp. 5202-5219, vol. 266, No. 8.

Tanimura, Akihiko, et al., Fluorescent Biosensor for Quantitative Real-time Measurements of Inositol 1,4,5-Trisphosphate in Single Living Cells, J. Biol. Chem., Sep. 10, 2004, pp. 38095-38098, vol. 279, No. 37.

\* cited by examiner

SEQUENCE LISTING

<160> NUMBER OF SEQ ID NOS: 39

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1
gatcgagctc gatggtgagc aagggcgagg                30

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
gatcgaattc atggtgagca agggcgagga                30

<210> SEQ ID NO 3
<211> LENGTH: 28
<212> TYPE: DNA
<213> ORGANISM: Artificial
<220> FEATURE:
<223> OTHER INFORMATION: primer

<400> SEQUENCE: 3
gatcggatcc atggtgagca agggcgag                  28

<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4
gatcaagctt gtacagctcg tccatgc                   27

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
gatcatatgg tgagcaaggg cgag                      24

<210> SEQ ID NO 6
<211> LENGTH: 43
<212> TYPE: DNA
<213> ORGANISM: Artificial
<220> FEATURE:
<223> OTHER INFORMATION: primer

<400> SEQUENCE: 6
gtttaccttc ttcgattttc atcttgtaca gctcgtccat gcc        43

<210> SEQ ID NO 7
<211> LENGTH: 41

<212> TYPE: DNA
<213> ORGANISM: Artificial
<220> FEATURE:
<223> OTHER INFORMATION: primer

<400> SEQUENCE: 7
gtttaccttc ttcgattttc atgcggccgc tttccttgta c            41

<210> SEQ ID NO 8
<211> LENGTH: 48
<212> TYPE: DNA
<213> ORGANISM: Artificial
<220> FEATURE:
<223> OTHER INFORMATION: primer

<400> SEQUENCE: 8
gtttaccttc ttcgattttc attcgcgact tgtacagctc gtccatgc     48

<210> SEQ ID NO 9
<211> LENGTH: 48
<212> TYPE: DNA
<213> ORGANISM: Artificial
<220> FEATURE:
<223> OTHER INFORMATION: primer

<400> SEQUENCE: 9
gtttaccttc ttcgattttc atgctagcct tgtacagctc gtccatgc     48

<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10
atgaaaatcg aagaaggtaa ac                                 22

<210> SEQ ID NO 11
<211> LENGTH: 28
<212> TYPE: DNA
<213> ORGANISM: Artificial
<220> FEATURE:
<223> OTHER INFORMATION: primer

<400> SEQUENCE: 11
gatcggatcc cgagctcgaa ttagtctg                           28

<210> SEQ ID NO 12
<211> LENGTH: 49
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (23)..(28)
<223> OTHER INFORMATION: n is a, c, g, or t

<400> SEQUENCE: 12
gtttaccttc ttcgattttc atnnnnnnct tgtacagctc gtccatgcc    49

<210> SEQ ID NO 13
<211> LENGTH: 37
<212> TYPE: DNA
<213> ORGANISM: Artificial
<220> FEATURE:

<223> OTHER INFORMATION: primer
<220> FEATURE:
<221> NAME/KEY: misc_feature
<222> LOCATION: (17)..(19)
<223> OTHER INFORMATION: n is a, c, g, or t

<400> SEQUENCE: 13
caaagcggtc gtgtgcnnng aagataatgt cagggcc                              37

<210> SEQ ID NO 14
<211> LENGTH: 49
<212> TYPE: DNA
<213> ORGANISM: Artificial
<220> FEATURE:
<223> OTHER INFORMATION: primer

<400> SEQUENCE: 14
gtttaccttc ttcgattttc atgtgtagct tgtacagctc gtccatgcc                 49

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
ctcttcccag gtttttggcg                                                 20

<210> SEQ ID NO 16
<211> LENGTH: 23
<212> TYPE: DNA
<213> ORGANISM: Artificial
<220> FEATURE:
<223> OTHER INFORMATION: primer

<400> SEQUENCE: 16
gggagctcat cgcttcgctg att                                             23

<210> SEQ ID NO 17
<211> LENGTH: 29
<212> TYPE: DNA
<213> ORGANISM: Artificial
<220> FEATURE:
<223> OTHER INFORMATION: primer

<400> SEQUENCE: 17
gcatatgtct tttgaattct tgaattttc                                       29

<210> SEQ ID NO 18
<211> LENGTH: 47
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (22)..(27)
<223> OTHER INFORMATION: n is a, c, g, or t

<400> SEQUENCE: 18
gacagcatat tcggcggcca tnnnnnnctt gtacagctcg tccatgc                   47

<210> SEQ ID NO 19
<211> LENGTH: 20
<212> TYPE: DNA
<213> ORGANISM: Artificial

```
<220> FEATURE:
<223> OTHER INFORMATION: primer

<400> SEQUENCE: 19
atggccgccg aatatgctgt                                              20

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
cgcggatccc gattgagtga ccaggatt                                     28

<210> SEQ ID NO 21
<211> LENGTH: 46
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (21)..(26)
<223> OTHER INFORMATION: n is a, c, g, or t

<400> SEQUENCE: 21
ccgagcttca ggttctccat nnnnnncttg tacagctcgt ccatgc                 46

<210> SEQ ID NO 22
<211> LENGTH: 19
<212> TYPE: DNA
<213> ORGANISM: Artificial
<220> FEATURE:
<223> OTHER INFORMATION: primer

<400> SEQUENCE: 22
atggagaacc tgaagctcg                                               19

<210> SEQ ID NO 23
<211> LENGTH: 29
<212> TYPE: DNA
<213> ORGANISM: Artificial
<220> FEATURE:
<223> OTHER INFORMATION: primer

<400> SEQUENCE: 23
cgcggatccc gacttaccgc ctaaacctt                                    29

<210> SEQ ID NO 24
<211> LENGTH: 48
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (23)..(28)
<223> OTHER INFORMATION: n is a, c, g, or t

<400> SEQUENCE: 24
ccagcgcgat ggtgtctttc atnnnnnnct tgtacagctc gtccatgc               48

<210> SEQ ID NO 25
<211> LENGTH: 18
<212> TYPE: DNA
```

```
<213> ORGANISM: Artificial
<220> FEATURE:
<223> OTHER INFORMATION: primer

<400> SEQUENCE: 25
atgaaagaca ccgcgctg                                                  18

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
cgcggatccc gactgcttaa caaccagttt                                     30

<210> SEQ ID NO 27
<211> LENGTH: 67
<212> TYPE: DNA
<213> ORGANISM: Artificial
<220> FEATURE:
<223> OTHER INFORMATION: primer

<400> SEQUENCE: 27
atgaaaatcg aagaaggtaa actggtaatc tggattaacg gcctgtttgg ctataacggt    60
ctcgctg                                                              67

<210> SEQ ID NO 28
<211> LENGTH: 41
<212> TYPE: DNA
<213> ORGANISM: Artificial
<220> FEATURE:
<223> OTHER INFORMATION: primer

<400> SEQUENCE: 28
caaagcggtc gtgtgcatag aagataatgt cagggccatc g                        41

<210> SEQ ID NO 29
<211> LENGTH: 40
<212> TYPE: DNA
<213> ORGANISM: Artificial
<220> FEATURE:
<223> OTHER INFORMATION: primer

<400> SEQUENCE: 29
aatcagcgat aacgcataaa cagcgatcgg gtaagcaatc                          40

<210> SEQ ID NO 30
<211> LENGTH: 370
<212> TYPE: PRT
<213> ORGANISM: Escherichia coli

<400> SEQUENCE: 30
```

Lys Ile Glu Glu Gly Lys Leu Val Ile Trp Ile Asn Gly Asp Lys Gly
 1               5                  10                  15

Tyr Asn Gly Leu Ala Glu Val Gly Lys Lys Phe Glu Lys Asp Thr Gly
                20                  25                  30

Ile Lys Val Thr Val Glu His Pro Asp Lys Leu Glu Glu Lys Phe Pro
            35                  40                  45

Gln Val Ala Ala Thr Gly Asp Gly Pro Asp Ile Ile Phe Trp Ala His
        50                  55                  60

Asp Arg Phe Gly Gly Tyr Ala Gln Ser Gly Leu Leu Ala Glu Ile Thr
65                  70                  75                  80

-continued

```
Pro Asp Lys Ala Phe Gln Asp Lys Leu Tyr Pro Phe Thr Trp Asp Ala
                 85                  90                  95
Val Arg Tyr Asn Gly Lys Leu Ile Ala Tyr Pro Ile Ala Val Glu Ala
                100                 105                 110
Leu Ser Leu Ile Tyr Asn Lys Asp Leu Leu Pro Asn Pro Pro Lys Thr
                115                 120                 125
Trp Glu Glu Ile Pro Ala Leu Asp Lys Glu Leu Lys Ala Lys Gly Lys
                130                 135                 140
Ser Ala Leu Met Phe Asn Leu Gln Glu Pro Tyr Phe Thr Trp Pro Leu
145                 150                 155                 160
Ile Ala Ala Asp Gly Gly Tyr Ala Phe Lys Tyr Glu Asn Gly Lys Tyr
                165                 170                 175
Asp Ile Lys Asp Val Gly Val Asp Asn Ala Gly Ala Lys Ala Gly Leu
                180                 185                 190
Thr Phe Leu Val Asp Leu Ile Lys Asn Lys His Met Asn Ala Asp Thr
                195                 200                 205
Asp Tyr Ser Ile Ala Glu Ala Ala Phe Asn Lys Gly Glu Thr Ala Met
                210                 215                 220
Thr Ile Asn Gly Pro Trp Ala Trp Ser Asn Ile Asp Thr Ser Lys Val
225                 230                 235                 240
Asn Tyr Gly Val Thr Val Leu Pro Thr Phe Lys Gly Gln Pro Ser Lys
                245                 250                 255
Pro Phe Val Gly Val Leu Ser Ala Gly Ile Asn Ala Ala Ser Pro Asn
                260                 265                 270
Lys Glu Leu Ala Lys Glu Phe Leu Glu Asn Tyr Leu Leu Thr Asp Glu
                275                 280                 285
Gly Leu Glu Ala Val Asn Lys Asp Lys Pro Leu Gly Ala Val Ala Leu
                290                 295                 300
Lys Ser Tyr Glu Glu Glu Leu Ala Lys Asp Pro Arg Ile Ala Ala Thr
305                 310                 315                 320
Met Glu Asn Ala Gln Lys Gly Glu Ile Met Pro Asn Ile Pro Gln Met
                325                 330                 335
Ser Ala Phe Trp Tyr Ala Val Arg Thr Ala Val Ile Asn Ala Ala Ser
                340                 345                 350
Gly Arg Gln Thr Val Asp Glu Ala Leu Lys Asp Ala Gln Thr Asn Ser
                355                 360                 365
Ser Ser
370

<210> SEQ ID NO 31
<211> LENGTH: 865
<212> TYPE: PRT
<213> ORGANISM: Artificial
<220> FEATURE:
<223> OTHER INFORMATION: CMY-QI

<400> SEQUENCE: 31

Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
                20                  25                  30
Glu Gly Glu Gly Asp Ala Thr Tyr Gly Lys Leu Thr Leu Lys Phe Ile
                35                  40                  45
Cys Thr Thr Gly Lys Leu Pro Val Pro Trp Pro Thr Leu Val Thr Thr
                50                  55                  60
```

-continued

```
Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Gln
225                 230                 235                 240

Ile Met Lys Ile Glu Glu Gly Lys Leu Val Ile Trp Ile Asn Gly Asp
                245                 250                 255

Lys Gly Tyr Asn Gly Leu Ala Glu Val Gly Lys Lys Phe Glu Lys Asp
            260                 265                 270

Thr Gly Ile Lys Val Thr Val Glu His Pro Asp Lys Leu Glu Glu Lys
        275                 280                 285

Phe Pro Gln Val Ala Ala Thr Gly Asp Gly Pro Asp Ile Ile Phe Trp
    290                 295                 300

Ala His Asp Arg Phe Gly Gly Tyr Ala Gln Ser Gly Leu Leu Ala Glu
305                 310                 315                 320

Ile Thr Pro Asp Lys Ala Phe Gln Asp Lys Leu Tyr Pro Phe Thr Trp
                325                 330                 335

Asp Ala Val Arg Tyr Asn Gly Lys Leu Ile Ala Tyr Pro Ile Ala Val
            340                 345                 350

Glu Ala Leu Ser Leu Ile Tyr Asn Lys Asp Leu Leu Pro Asn Pro Pro
        355                 360                 365

Lys Thr Trp Glu Glu Ile Pro Ala Leu Asp Lys Glu Leu Lys Ala Lys
    370                 375                 380

Gly Lys Ser Ala Leu Met Phe Asn Leu Gln Glu Pro Tyr Phe Thr Trp
385                 390                 395                 400

Pro Leu Ile Ala Ala Asp Gly Gly Tyr Ala Phe Lys Tyr Glu Asn Gly
                405                 410                 415

Lys Tyr Asp Ile Lys Asp Val Gly Val Asp Asn Ala Gly Ala Lys Ala
            420                 425                 430

Gly Leu Thr Phe Leu Val Asp Leu Ile Lys Asn Lys His Met Asn Ala
        435                 440                 445

Asp Thr Asp Tyr Ser Ile Ala Glu Ala Ala Phe Asn Lys Gly Glu Thr
    450                 455                 460

Ala Met Thr Ile Asn Gly Pro Trp Ala Trp Ser Asn Ile Asp Thr Ser
465                 470                 475                 480
```

```
Lys Val Asn Tyr Gly Val Thr Val Leu Pro Thr Phe Lys Gly Gln Pro
            485                 490                 495

Ser Lys Pro Phe Val Gly Val Leu Ser Ala Gly Ile Asn Ala Ala Ser
            500                 505                 510

Pro Asn Lys Glu Leu Ala Lys Glu Phe Leu Glu Asn Tyr Leu Leu Thr
            515                 520                 525

Asp Glu Gly Leu Glu Ala Val Asn Lys Asp Lys Pro Leu Gly Ala Val
            530                 535                 540

Ala Leu Lys Ser Tyr Glu Glu Leu Ala Lys Asp Pro Arg Ile Ala
545                 550                 555                 560

Ala Thr Met Glu Asn Ala Gln Lys Gly Glu Ile Met Pro Asn Ile Pro
                565                 570                 575

Gln Met Ser Ala Phe Trp Tyr Ala Val Arg Thr Ala Val Ile Asn Ala
            580                 585                 590

Ala Ser Gly Arg Gln Thr Val Asp Glu Ala Leu Lys Asp Ala Gln Thr
            595                 600                 605

Asn Ser Ser Ser Gly Ser Met Val Ser Lys Gly Glu Glu Leu Phe Thr
            610                 615                 620

Gly Val Val Pro Ile Leu Val Glu Leu Asp Gly Asp Val Asn Gly His
625                 630                 635                 640

Lys Phe Ser Val Ser Gly Glu Gly Glu Gly Asp Ala Thr Tyr Gly Lys
                645                 650                 655

Leu Thr Leu Lys Phe Ile Cys Thr Thr Gly Lys Leu Pro Val Pro Trp
            660                 665                 670

Pro Thr Leu Val Thr Thr Phe Gly Tyr Gly Leu Gln Cys Phe Ala Arg
            675                 680                 685

Tyr Pro Asp His Met Lys Gln His Asp Phe Phe Lys Ser Ala Met Pro
            690                 695                 700

Glu Gly Tyr Val Gln Glu Arg Thr Ile Phe Phe Lys Asp Asp Gly Asn
705                 710                 715                 720

Tyr Lys Thr Arg Ala Glu Val Lys Phe Glu Gly Asp Thr Leu Val Asn
                725                 730                 735

Arg Ile Glu Leu Lys Gly Ile Asp Phe Lys Glu Asp Gly Asn Ile Leu
            740                 745                 750

Gly His Lys Leu Glu Tyr Asn Tyr Asn Ser His Asn Val Tyr Ile Met
            755                 760                 765

Ala Asp Lys Gln Lys Asn Gly Ile Lys Val Asn Phe Lys Ile Arg His
    770                 775                 780

Asn Ile Glu Asp Gly Ser Val Gln Leu Ala Asp His Tyr Gln Gln Asn
785                 790                 795                 800

Thr Pro Ile Gly Asp Gly Pro Val Leu Leu Pro Asp Asn His Tyr Leu
                805                 810                 815

Ser Tyr Gln Ser Ala Leu Ser Lys Asp Pro Asn Glu Lys Arg Asp His
            820                 825                 830

Met Val Leu Leu Glu Phe Val Thr Ala Ala Gly Ile Thr Leu Gly Met
            835                 840                 845

Asp Glu Leu Tyr Lys Leu Ala Ala Ala Leu Glu His His His His His
    850                 855                 860

His
865

<210> SEQ ID NO 32
<211> LENGTH: 865
<212> TYPE: PRT
```

-continued

```
<213> ORGANISM: Artificial
<220> FEATURE:
<223> OTHER INFORMATION: CMY-LH

<400> SEQUENCE: 32

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Leu
225                 230                 235                 240

His Met Lys Ile Glu Glu Gly Lys Leu Val Ile Trp Ile Asn Gly Asp
                245                 250                 255

Lys Gly Tyr Asn Gly Leu Ala Glu Val Gly Lys Lys Phe Glu Lys Asp
            260                 265                 270

Thr Gly Ile Lys Val Thr Val Glu His Pro Asp Lys Leu Glu Glu Lys
        275                 280                 285

Phe Pro Gln Val Ala Ala Thr Gly Asp Gly Pro Asp Ile Ile Phe Trp
290                 295                 300

Ala His Asp Arg Phe Gly Gly Tyr Ala Gln Ser Gly Leu Leu Ala Glu
305                 310                 315                 320

Ile Thr Pro Asp Lys Ala Phe Gln Asp Lys Leu Tyr Pro Phe Thr Trp
                325                 330                 335

Asp Ala Val Arg Tyr Asn Gly Lys Leu Ile Ala Tyr Pro Ile Ala Val
            340                 345                 350

Glu Ala Leu Ser Leu Ile Tyr Asn Lys Asp Leu Leu Pro Asn Pro Pro
        355                 360                 365

Lys Thr Trp Glu Glu Ile Pro Ala Leu Asp Lys Glu Leu Lys Ala Lys
370                 375                 380
```

-continued

```
Gly Lys Ser Ala Leu Met Phe Asn Leu Gln Glu Pro Tyr Phe Thr Trp
385                 390                 395                 400

Pro Leu Ile Ala Ala Asp Gly Gly Tyr Ala Phe Lys Tyr Glu Asn Gly
            405                 410                 415

Lys Tyr Asp Ile Lys Asp Val Gly Val Asp Asn Ala Gly Ala Lys Ala
                420                 425                 430

Gly Leu Thr Phe Leu Val Asp Leu Ile Lys Asn Lys His Met Asn Ala
            435                 440                 445

Asp Thr Asp Tyr Ser Ile Ala Glu Ala Ala Phe Asn Lys Gly Glu Thr
            450                 455                 460

Ala Met Thr Ile Asn Gly Pro Trp Ala Trp Ser Asn Ile Asp Thr Ser
465                 470                 475                 480

Lys Val Asn Tyr Gly Val Thr Val Leu Pro Thr Phe Lys Gly Gln Pro
                485                 490                 495

Ser Lys Pro Phe Val Gly Val Leu Ser Ala Gly Ile Asn Ala Ala Ser
            500                 505                 510

Pro Asn Lys Glu Leu Ala Lys Glu Phe Leu Glu Asn Tyr Leu Leu Thr
            515                 520                 525

Asp Glu Gly Leu Glu Ala Val Asn Lys Asp Lys Pro Leu Gly Ala Val
            530                 535                 540

Ala Leu Lys Ser Tyr Glu Glu Leu Ala Lys Asp Pro Arg Ile Ala
545                 550                 555                 560

Ala Thr Met Glu Asn Ala Gln Lys Gly Glu Ile Met Pro Asn Ile Pro
                565                 570                 575

Gln Met Ser Ala Phe Trp Tyr Ala Val Arg Thr Ala Val Ile Asn Ala
            580                 585                 590

Ala Ser Gly Arg Gln Thr Val Asp Glu Ala Leu Lys Asp Ala Gln Thr
            595                 600                 605

Asn Ser Ser Ser Gly Ser Met Val Ser Lys Gly Glu Glu Leu Phe Thr
            610                 615                 620

Gly Val Val Pro Ile Leu Val Glu Leu Asp Gly Asp Val Asn Gly His
625                 630                 635                 640

Lys Phe Ser Val Ser Gly Glu Gly Glu Gly Asp Ala Thr Tyr Gly Lys
                645                 650                 655

Leu Thr Leu Lys Phe Ile Cys Thr Thr Gly Lys Leu Pro Val Pro Trp
            660                 665                 670

Pro Thr Leu Val Thr Thr Phe Gly Tyr Gly Leu Gln Cys Phe Ala Arg
            675                 680                 685

Tyr Pro Asp His Met Lys Gln His Asp Phe Phe Lys Ser Ala Met Pro
            690                 695                 700

Glu Gly Tyr Val Gln Glu Arg Thr Ile Phe Phe Lys Asp Asp Gly Asn
705                 710                 715                 720

Tyr Lys Thr Arg Ala Glu Val Lys Phe Glu Gly Asp Thr Leu Val Asn
                725                 730                 735

Arg Ile Glu Leu Lys Gly Ile Asp Phe Lys Glu Asp Gly Asn Ile Leu
            740                 745                 750

Gly His Lys Leu Glu Tyr Asn Tyr Asn Ser His Asn Val Tyr Ile Met
            755                 760                 765

Ala Asp Lys Gln Lys Asn Gly Ile Lys Val Asn Phe Lys Ile Arg His
            770                 775                 780

Asn Ile Glu Asp Gly Ser Val Gln Leu Ala Asp His Tyr Gln Gln Asn
785                 790                 795                 800
```

-continued

```
Thr Pro Ile Gly Asp Gly Pro Val Leu Leu Pro Asp Asn His Tyr Leu
                805                 810                 815

Ser Tyr Gln Ser Ala Leu Ser Lys Asp Pro Asn Glu Lys Arg Asp His
                820                 825                 830

Met Val Leu Leu Glu Phe Val Thr Ala Ala Gly Ile Thr Leu Gly Met
                835                 840                 845

Asp Glu Leu Tyr Lys Leu Ala Ala Ala Leu Glu His His His His
    850                 855                 860

His
865

<210> SEQ ID NO 33
<211> LENGTH: 865
<212> TYPE: PRT
<213> ORGANISM: Artificial
<220> FEATURE:
<223> OTHER INFORMATION: CMY-LH/W62A

<400> SEQUENCE: 33

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys Leu
225                 230                 235                 240

His Met Lys Ile Glu Glu Gly Lys Leu Val Ile Trp Ile Asn Gly Asp
                245                 250                 255

Lys Gly Tyr Asn Gly Leu Ala Glu Val Gly Lys Lys Phe Glu Lys Asp
                260                 265                 270

Thr Gly Ile Lys Val Thr Val Glu His Pro Asp Lys Leu Glu Glu Lys
            275                 280                 285
```

-continued

```
Phe Pro Gln Val Ala Ala Thr Gly Asp Gly Pro Asp Ile Ile Phe Ala
    290                 295                 300
Ala His Asp Arg Phe Gly Gly Tyr Ala Gln Ser Gly Leu Leu Ala Glu
305                 310                 315                 320
Ile Thr Pro Asp Lys Ala Phe Gln Asp Lys Leu Tyr Pro Phe Thr Trp
                325                 330                 335
Asp Ala Val Arg Tyr Asn Gly Lys Leu Ile Ala Tyr Pro Ile Ala Val
            340                 345                 350
Glu Ala Leu Ser Leu Ile Tyr Asn Lys Asp Leu Leu Pro Asn Pro Pro
        355                 360                 365
Lys Thr Trp Glu Glu Ile Pro Ala Leu Asp Lys Glu Leu Lys Ala Lys
370                 375                 380
Gly Lys Ser Ala Leu Met Phe Asn Leu Gln Glu Pro Tyr Phe Thr Trp
385                 390                 395                 400
Pro Leu Ile Ala Ala Asp Gly Gly Tyr Ala Phe Lys Tyr Glu Asn Gly
                405                 410                 415
Lys Tyr Asp Ile Lys Asp Val Gly Val Asp Asn Ala Gly Ala Lys Ala
            420                 425                 430
Gly Leu Thr Phe Leu Val Asp Leu Ile Lys Asn Lys His Met Asn Ala
        435                 440                 445
Asp Thr Asp Tyr Ser Ile Ala Glu Ala Ala Phe Asn Lys Gly Glu Thr
    450                 455                 460
Ala Met Thr Ile Asn Gly Pro Trp Ala Trp Ser Asn Ile Asp Thr Ser
465                 470                 475                 480
Lys Val Asn Tyr Gly Val Thr Val Leu Pro Thr Phe Lys Gly Gln Pro
                485                 490                 495
Ser Lys Pro Phe Val Gly Val Leu Ser Ala Gly Ile Asn Ala Ala Ser
            500                 505                 510
Pro Asn Lys Glu Leu Ala Lys Glu Phe Leu Glu Asn Tyr Leu Leu Thr
        515                 520                 525
Asp Glu Gly Leu Glu Ala Val Asn Lys Asp Lys Pro Leu Gly Ala Val
    530                 535                 540
Ala Leu Lys Ser Tyr Glu Glu Leu Ala Lys Asp Pro Arg Ile Ala
545                 550                 555                 560
Ala Thr Met Glu Asn Ala Gln Lys Gly Glu Ile Met Pro Asn Ile Pro
                565                 570                 575
Gln Met Ser Ala Phe Trp Tyr Ala Val Arg Thr Ala Val Ile Asn Ala
            580                 585                 590
Ala Ser Gly Arg Gln Thr Val Asp Glu Ala Leu Lys Asp Ala Gln Thr
        595                 600                 605
Asn Ser Ser Gly Ser Met Val Ser Lys Gly Glu Glu Leu Phe Thr
    610                 615                 620
Gly Val Val Pro Ile Leu Val Glu Leu Asp Gly Asp Val Asn Gly His
625                 630                 635                 640
Lys Phe Ser Val Ser Gly Glu Gly Glu Gly Asp Ala Thr Tyr Gly Lys
                645                 650                 655
Leu Thr Leu Lys Phe Ile Cys Thr Thr Gly Lys Leu Pro Val Pro Trp
            660                 665                 670
Pro Thr Leu Val Thr Thr Phe Gly Tyr Gly Leu Gln Cys Phe Ala Arg
        675                 680                 685
Tyr Pro Asp His Met Lys Gln His Asp Phe Phe Lys Ser Ala Met Pro
    690                 695                 700
```

```
Glu Gly Tyr Val Gln Glu Arg Thr Ile Phe Phe Lys Asp Asp Gly Asn
705                 710                 715                 720

Tyr Lys Thr Arg Ala Glu Val Lys Phe Glu Gly Asp Thr Leu Val Asn
            725                 730                 735

Arg Ile Glu Leu Lys Gly Ile Asp Phe Lys Glu Asp Gly Asn Ile Leu
        740                 745                 750

Gly His Lys Leu Glu Tyr Asn Tyr Asn Ser His Asn Val Tyr Ile Met
    755                 760                 765

Ala Asp Lys Gln Lys Asn Gly Ile Lys Val Asn Phe Lys Ile Arg His
770                 775                 780

Asn Ile Glu Asp Gly Ser Val Gln Leu Ala Asp His Tyr Gln Gln Asn
785                 790                 795                 800

Thr Pro Ile Gly Asp Gly Pro Val Leu Leu Pro Asp Asn His Tyr Leu
            805                 810                 815

Ser Tyr Gln Ser Ala Leu Ser Lys Asp Pro Asn Glu Lys Arg Asp His
        820                 825                 830

Met Val Leu Leu Glu Phe Val Thr Ala Ala Gly Ile Thr Leu Gly Met
    835                 840                 845

Asp Glu Leu Tyr Lys Leu Ala Ala Ala Leu Glu His His His His His
850                 855                 860

His
865

<210> SEQ ID NO 34
<211> LENGTH: 865
<212> TYPE: PRT
<213> ORGANISM: Artificial
<220> FEATURE:
<223> OTHER INFORMATION: CMY-LH/W62H

<400> SEQUENCE: 34

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Leu
225                 230                 235                 240

His Met Lys Ile Glu Glu Gly Lys Leu Val Ile Trp Ile Asn Gly Asp
                245                 250                 255

Lys Gly Tyr Asn Gly Leu Ala Glu Val Gly Lys Lys Phe Glu Lys Asp
            260                 265                 270

Thr Gly Ile Lys Val Thr Val Glu His Pro Asp Lys Leu Glu Glu Lys
        275                 280                 285

Phe Pro Gln Val Ala Ala Thr Gly Asp Gly Pro Asp Ile Ile Phe His
290                 295                 300

Ala His Asp Arg Phe Gly Gly Tyr Ala Gln Ser Gly Leu Leu Ala Glu
305                 310                 315                 320

Ile Thr Pro Asp Lys Ala Phe Gln Asp Lys Leu Tyr Pro Phe Thr Trp
                325                 330                 335

Asp Ala Val Arg Tyr Asn Gly Lys Leu Ile Ala Tyr Pro Ile Ala Val
            340                 345                 350

Glu Ala Leu Ser Leu Ile Tyr Asn Lys Asp Leu Leu Pro Asn Pro Pro
        355                 360                 365

Lys Thr Trp Glu Glu Ile Pro Ala Leu Asp Lys Glu Leu Lys Ala Lys
    370                 375                 380

Gly Lys Ser Ala Leu Met Phe Asn Leu Gln Glu Pro Tyr Phe Thr Trp
385                 390                 395                 400

Pro Leu Ile Ala Ala Asp Gly Gly Tyr Ala Phe Lys Tyr Glu Asn Gly
                405                 410                 415

Lys Tyr Asp Ile Lys Asp Val Gly Val Asp Asn Ala Gly Ala Lys Ala
            420                 425                 430

Gly Leu Thr Phe Leu Val Asp Leu Ile Lys Asn Lys His Met Asn Ala
        435                 440                 445

Asp Thr Asp Tyr Ser Ile Ala Glu Ala Ala Phe Asn Lys Gly Glu Thr
    450                 455                 460

Ala Met Thr Ile Asn Gly Pro Trp Ala Trp Ser Asn Ile Asp Thr Ser
465                 470                 475                 480

Lys Val Asn Tyr Gly Val Thr Val Leu Pro Thr Phe Lys Gly Gln Pro
                485                 490                 495

Ser Lys Pro Phe Val Gly Val Leu Ser Ala Gly Ile Asn Ala Ala Ser
            500                 505                 510

Pro Asn Lys Glu Leu Ala Lys Glu Phe Leu Glu Asn Tyr Leu Leu Thr
        515                 520                 525

Asp Glu Gly Leu Glu Ala Val Asn Lys Asp Lys Pro Leu Gly Ala Val
    530                 535                 540

Ala Leu Lys Ser Tyr Glu Glu Leu Ala Lys Asp Pro Arg Ile Ala
545                 550                 555                 560

Ala Thr Met Glu Asn Ala Gln Lys Gly Glu Ile Met Pro Asn Ile Pro
                565                 570                 575

Gln Met Ser Ala Phe Trp Tyr Ala Val Arg Thr Ala Val Ile Asn Ala
            580                 585                 590

Ala Ser Gly Arg Gln Thr Val Asp Glu Ala Leu Lys Asp Ala Gln Thr
        595                 600                 605
```

```
Asn Ser Ser Ser Gly Ser Met Val Ser Lys Gly Glu Glu Leu Phe Thr
        610                 615                 620

Gly Val Val Pro Ile Leu Val Glu Leu Asp Gly Asp Val Asn Gly His
625                 630                 635                 640

Lys Phe Ser Val Ser Gly Glu Gly Glu Gly Asp Ala Thr Tyr Gly Lys
            645                 650                 655

Leu Thr Leu Lys Phe Ile Cys Thr Thr Gly Lys Leu Pro Val Pro Trp
            660                 665                 670

Pro Thr Leu Val Thr Thr Phe Gly Tyr Gly Leu Gln Cys Phe Ala Arg
            675                 680                 685

Tyr Pro Asp His Met Lys Gln His Asp Phe Phe Lys Ser Ala Met Pro
690                 695                 700

Glu Gly Tyr Val Gln Glu Arg Thr Ile Phe Phe Lys Asp Asp Gly Asn
705                 710                 715                 720

Tyr Lys Thr Arg Ala Glu Val Lys Phe Glu Gly Asp Thr Leu Val Asn
            725                 730                 735

Arg Ile Glu Leu Lys Gly Ile Asp Phe Lys Glu Asp Gly Asn Ile Leu
            740                 745                 750

Gly His Lys Leu Glu Tyr Asn Tyr Asn Ser His Asn Val Tyr Ile Met
            755                 760                 765

Ala Asp Lys Gln Lys Asn Gly Ile Lys Val Asn Phe Lys Ile Arg His
770                 775                 780

Asn Ile Glu Asp Gly Ser Val Gln Leu Ala Asp His Tyr Gln Gln Asn
785                 790                 795                 800

Thr Pro Ile Gly Asp Gly Pro Val Leu Leu Pro Asp Asn His Tyr Leu
            805                 810                 815

Ser Tyr Gln Ser Ala Leu Ser Lys Asp Pro Asn Glu Lys Arg Asp His
            820                 825                 830

Met Val Leu Leu Glu Phe Val Thr Ala Ala Gly Ile Thr Leu Gly Met
            835                 840                 845

Asp Glu Leu Tyr Lys Leu Ala Ala Ala Leu Glu His His His His His
    850                 855                 860

His
865

<210> SEQ ID NO 35
<211> LENGTH: 865
<212> TYPE: PRT
<213> ORGANISM: Artificial
<220> FEATURE:
<223> OTHER INFORMATION: CMY-LH/W62L

<400> SEQUENCE: 35

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

-continued

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Leu
225                 230                 235                 240

His Met Lys Ile Glu Glu Gly Lys Leu Val Ile Trp Ile Asn Gly Asp
                245                 250                 255

Lys Gly Tyr Asn Gly Leu Ala Glu Val Gly Lys Lys Phe Glu Lys Asp
            260                 265                 270

Thr Gly Ile Lys Val Thr Val Glu His Pro Asp Lys Leu Glu Glu Lys
        275                 280                 285

Phe Pro Gln Val Ala Ala Thr Gly Asp Gly Pro Asp Ile Ile Phe Leu
    290                 295                 300

Ala His Asp Arg Phe Gly Gly Tyr Ala Gln Ser Gly Leu Leu Ala Glu
305                 310                 315                 320

Ile Thr Pro Asp Lys Ala Phe Gln Asp Lys Leu Tyr Pro Phe Thr Trp
                325                 330                 335

Asp Ala Val Arg Tyr Asn Gly Lys Leu Ile Ala Tyr Pro Ile Ala Val
            340                 345                 350

Glu Ala Leu Ser Leu Ile Tyr Asn Lys Asp Leu Leu Pro Asn Pro Pro
        355                 360                 365

Lys Thr Trp Glu Glu Ile Pro Ala Leu Asp Lys Glu Leu Lys Ala Lys
    370                 375                 380

Gly Lys Ser Ala Leu Met Phe Asn Leu Gln Glu Pro Tyr Phe Thr Trp
385                 390                 395                 400

Pro Leu Ile Ala Ala Asp Gly Gly Tyr Ala Phe Lys Tyr Glu Asn Gly
                405                 410                 415

Lys Tyr Asp Ile Lys Asp Val Gly Val Asp Asn Ala Gly Ala Lys Ala
            420                 425                 430

Gly Leu Thr Phe Leu Val Asp Leu Ile Lys Asn Lys His Met Asn Ala
        435                 440                 445

Asp Thr Asp Tyr Ser Ile Ala Glu Ala Ala Phe Asn Lys Gly Glu Thr
    450                 455                 460

Ala Met Thr Ile Asn Gly Pro Trp Ala Trp Ser Asn Ile Asp Thr Ser
465                 470                 475                 480

Lys Val Asn Tyr Gly Val Thr Val Leu Pro Thr Phe Lys Gly Gln Pro
                485                 490                 495

Ser Lys Pro Phe Val Gly Val Leu Ser Ala Gly Ile Asn Ala Ala Ser
            500                 505                 510
```

Pro Asn Lys Glu Leu Ala Lys Glu Phe Leu Glu Asn Tyr Leu Leu Thr
    515                 520                 525

Asp Glu Gly Leu Glu Ala Val Asn Lys Asp Lys Pro Leu Gly Ala Val
530                 535                 540

Ala Leu Lys Ser Tyr Glu Glu Leu Ala Lys Asp Pro Arg Ile Ala
545                 550                 555                 560

Ala Thr Met Glu Asn Ala Gln Lys Gly Glu Ile Met Pro Asn Ile Pro
                565                 570                 575

Gln Met Ser Ala Phe Trp Tyr Ala Val Arg Thr Ala Val Ile Asn Ala
            580                 585                 590

Ala Ser Gly Arg Gln Thr Val Asp Glu Ala Leu Lys Asp Ala Gln Thr
        595                 600                 605

Asn Ser Ser Ser Gly Ser Met Val Ser Lys Gly Glu Glu Leu Phe Thr
    610                 615                 620

Gly Val Val Pro Ile Leu Val Glu Leu Asp Gly Asp Val Asn Gly His
625                 630                 635                 640

Lys Phe Ser Val Ser Gly Glu Gly Glu Gly Asp Ala Thr Tyr Gly Lys
                645                 650                 655

Leu Thr Leu Lys Phe Ile Cys Thr Thr Gly Lys Leu Pro Val Pro Trp
            660                 665                 670

Pro Thr Leu Val Thr Thr Phe Gly Tyr Gly Leu Gln Cys Phe Ala Arg
        675                 680                 685

Tyr Pro Asp His Met Lys Gln His Asp Phe Phe Lys Ser Ala Met Pro
    690                 695                 700

Glu Gly Tyr Val Gln Glu Arg Thr Ile Phe Phe Lys Asp Asp Gly Asn
705                 710                 715                 720

Tyr Lys Thr Arg Ala Glu Val Lys Phe Glu Gly Asp Thr Leu Val Asn
                725                 730                 735

Arg Ile Glu Leu Lys Gly Ile Asp Phe Lys Glu Asp Gly Asn Ile Leu
            740                 745                 750

Gly His Lys Leu Glu Tyr Asn Tyr Asn Ser His Asn Val Tyr Ile Met
        755                 760                 765

Ala Asp Lys Gln Lys Asn Gly Ile Lys Val Asn Phe Lys Ile Arg His
    770                 775                 780

Asn Ile Glu Asp Gly Ser Val Gln Leu Ala Asp His Tyr Gln Gln Asn
785                 790                 795                 800

Thr Pro Ile Gly Asp Gly Pro Val Leu Leu Pro Asp Asn His Tyr Leu
                805                 810                 815

Ser Tyr Gln Ser Ala Leu Ser Lys Asp Pro Asn Glu Lys Arg Asp His
            820                 825                 830

Met Val Leu Leu Glu Phe Val Thr Ala Ala Gly Ile Thr Leu Gly Met
        835                 840                 845

Asp Glu Leu Tyr Lys Leu Ala Ala Ala Leu Glu His His His His
    850                 855                 860

His
865

<210> SEQ ID NO 36
<211> LENGTH: 784
<212> TYPE: PRT
<213> ORGANISM: Artificial
<220> FEATURE:
<223> OTHER INFORMATION: CalsBY-QV

<400> SEQUENCE: 36

-continued

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                      55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Gln
225                 230                 235                 240

Val Met Ala Ala Glu Tyr Ala Val Leu Lys Thr Leu Ser Asn Pro
                245                 250                 255

Phe Trp Val Asp Met Lys Lys Gly Ile Glu Asp Glu Ala Lys Thr Leu
                260                 265                 270

Gly Val Ser Val Asp Ile Phe Ala Ser Pro Ser Glu Gly Asp Phe Gln
            275                 280                 285

Ser Gln Leu Gln Leu Phe Glu Asp Leu Ser Asn Lys Asn Tyr Lys Gly
        290                 295                 300

Ile Ala Phe Ala Pro Leu Ser Ser Val Asn Leu Val Met Pro Val Ala
305                 310                 315                 320

Arg Ala Trp Lys Lys Gly Ile Tyr Leu Val Asn Leu Asp Glu Lys Ile
                325                 330                 335

Asp Met Asp Asn Leu Lys Lys Ala Gly Gly Asn Val Glu Ala Phe Val
            340                 345                 350

Thr Thr Asp Asn Val Ala Val Gly Ala Lys Gly Ala Ser Phe Ile Ile
        355                 360                 365

Asp Lys Leu Gly Ala Glu Gly Glu Val Ala Ile Ile Glu Gly Lys
370                 375                 380

Ala Gly Asn Ala Ser Gly Glu Ala Arg Arg Asn Gly Ala Thr Glu Ala
385                 390                 395                 400

Phe Lys Lys Ala Ser Gln Ile Lys Leu Val Ala Ser Gln Pro Ala Asp
                405                 410                 415
```

-continued

```
Trp Asp Arg Ile Lys Ala Leu Asp Val Ala Thr Asn Val Leu Gln Arg
            420                 425                 430

Asn Pro Asn Ile Lys Ala Ile Tyr Cys Ala Asn Asp Thr Met Ala Met
        435                 440                 445

Gly Val Ala Gln Ala Val Ala Asn Ala Gly Lys Thr Gly Lys Val Leu
    450                 455                 460

Val Val Gly Thr Asp Gly Ile Pro Glu Ala Arg Lys Met Val Glu Ala
465                 470                 475                 480

Gly Gln Met Thr Ala Thr Val Ala Gln Asn Pro Ala Asp Ile Gly Ala
                485                 490                 495

Thr Gly Leu Lys Leu Met Val Asp Ala Glu Lys Ser Gly Lys Val Ile
            500                 505                 510

Pro Leu Asp Lys Ala Pro Glu Phe Lys Leu Val Asp Ser Ile Leu Val
        515                 520                 525

Thr Gln Ser Gly Ser Met Val Ser Lys Gly Glu Glu Leu Phe Thr Gly
    530                 535                 540

Val Val Pro Ile Leu Val Glu Leu Asp Gly Asp Val Asn Gly His Lys
545                 550                 555                 560

Phe Ser Val Ser Gly Glu Gly Glu Gly Asp Ala Thr Tyr Gly Lys Leu
                565                 570                 575

Thr Leu Lys Phe Ile Cys Thr Thr Gly Lys Leu Pro Val Pro Trp Pro
            580                 585                 590

Thr Leu Val Thr Thr Phe Gly Tyr Gly Leu Gln Cys Phe Ala Arg Tyr
        595                 600                 605

Pro Asp His Met Lys Gln His Asp Phe Phe Lys Ser Ala Met Pro Glu
    610                 615                 620

Gly Tyr Val Gln Glu Arg Thr Ile Phe Phe Lys Asp Asp Gly Asn Tyr
625                 630                 635                 640

Lys Thr Arg Ala Glu Val Lys Phe Glu Gly Asp Thr Leu Val Asn Arg
                645                 650                 655

Ile Glu Leu Lys Gly Ile Asp Phe Lys Glu Asp Gly Asn Ile Leu Gly
            660                 665                 670

His Lys Leu Glu Tyr Asn Tyr Asn Ser His Asn Val Tyr Ile Met Ala
        675                 680                 685

Asp Lys Gln Lys Asn Gly Ile Lys Val Asn Phe Lys Ile Arg His Asn
    690                 695                 700

Ile Glu Asp Gly Ser Val Gln Leu Ala Asp His Tyr Gln Gln Asn Thr
705                 710                 715                 720

Pro Ile Gly Asp Gly Pro Val Leu Leu Pro Asp Asn His Tyr Leu Ser
                725                 730                 735

Tyr Gln Ser Ala Leu Ser Lys Asp Pro Asn Glu Lys Arg Asp His Met
            740                 745                 750

Val Leu Leu Glu Phe Val Thr Ala Ala Gly Ile Thr Leu Gly Met Asp
        755                 760                 765

Glu Leu Tyr Lys Leu Ala Ala Ala Leu Glu His His His His His His
    770                 775                 780
```

<210> SEQ ID NO 37
<211> LENGTH: 802
<212> TYPE: PRT
<213> ORGANISM: Artificial
<220> FEATURE:
<223> OTHER INFORMATION: CaraFY-PR

<400> SEQUENCE: 37

-continued

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Pro
225                 230                 235                 240

Arg Met Glu Asn Leu Lys Leu Gly Phe Leu Val Lys Gln Pro Glu Glu
                245                 250                 255

Pro Trp Phe Gln Thr Glu Trp Lys Phe Ala Asp Lys Ala Gly Lys Asp
            260                 265                 270

Leu Gly Phe Glu Val Ile Lys Ile Ala Val Pro Asp Gly Glu Lys Thr
        275                 280                 285

Leu Asn Ala Ile Asp Ser Leu Ala Ala Ser Gly Ala Lys Gly Phe Val
    290                 295                 300

Ile Cys Thr Pro Asp Pro Lys Leu Gly Ser Ala Ile Val Ala Lys Ala
305                 310                 315                 320

Arg Gly Tyr Asp Met Lys Val Ile Ala Val Asp Asp Gln Phe Val Asn
                325                 330                 335

Ala Lys Gly Lys Pro Met Asp Thr Val Pro Leu Val Met Met Ala Ala
            340                 345                 350

Thr Lys Ile Gly Glu Arg Gln Gly Gln Glu Leu Tyr Lys Glu Met Gln
        355                 360                 365

Lys Arg Gly Trp Asp Val Lys Glu Ser Ala Val Met Ala Ile Thr Ala
    370                 375                 380

Asn Glu Leu Asp Thr Ala Arg Arg Thr Thr Gly Ser Met Asp Ala
385                 390                 395                 400

Leu Lys Ala Ala Gly Phe Pro Glu Lys Gln Ile Tyr Gln Val Pro Thr
            405                 410                 415

Lys Ser Asn Asp Ile Pro Gly Ala Phe Asp Ala Ala Asn Ser Met Leu
        420                 425                 430
```

```
Val Gln His Pro Glu Val Lys His Trp Leu Ile Val Gly Met Asn Asp
        435                 440                 445

Ser Thr Val Leu Gly Gly Val Arg Ala Thr Glu Gly Gln Gly Phe Lys
    450                 455                 460

Ala Ala Asp Ile Ile Gly Ile Gly Ile Asn Gly Val Asp Ala Val Ser
465                 470                 475                 480

Glu Leu Ser Lys Ala Gln Ala Thr Gly Phe Tyr Gly Ser Leu Leu Pro
                485                 490                 495

Ser Pro Asp Val His Gly Tyr Lys Ser Ser Glu Met Leu Tyr Asn Trp
            500                 505                 510

Val Ala Lys Asp Val Glu Pro Pro Lys Phe Thr Glu Val Thr Asp Val
        515                 520                 525

Val Leu Ile Thr Arg Asp Asn Phe Lys Glu Leu Glu Lys Lys Gly
        530                 535                 540

Leu Gly Gly Lys Ser Gly Ser Met Val Ser Lys Gly Glu Glu Leu Phe
545                 550                 555                 560

Thr Gly Val Val Pro Ile Leu Val Glu Leu Asp Gly Asp Val Asn Gly
                565                 570                 575

His Lys Phe Ser Val Ser Gly Glu Gly Glu Gly Asp Ala Thr Tyr Gly
                580                 585                 590

Lys Leu Thr Leu Lys Phe Ile Cys Thr Thr Gly Lys Leu Pro Val Pro
            595                 600                 605

Trp Pro Thr Leu Val Thr Thr Phe Gly Tyr Gly Leu Gln Cys Phe Ala
        610                 615                 620

Arg Tyr Pro Asp His Met Lys Gln His Asp Phe Phe Lys Ser Ala Met
625                 630                 635                 640

Pro Glu Gly Tyr Val Gln Glu Arg Thr Ile Phe Phe Lys Asp Asp Gly
                645                 650                 655

Asn Tyr Lys Thr Arg Ala Glu Val Lys Phe Glu Gly Asp Thr Leu Val
            660                 665                 670

Asn Arg Ile Glu Leu Lys Gly Ile Asp Phe Lys Glu Asp Gly Asn Ile
        675                 680                 685

Leu Gly His Lys Leu Glu Tyr Asn Tyr Asn Ser His Asn Val Tyr Ile
690                 695                 700

Met Ala Asp Lys Gln Lys Asn Gly Ile Lys Val Asn Phe Lys Ile Arg
705                 710                 715                 720

His Asn Ile Glu Asp Gly Ser Val Gln Leu Ala Asp His Tyr Gln Gln
                725                 730                 735

Asn Thr Pro Ile Gly Asp Gly Pro Val Leu Leu Pro Asp Asn His Tyr
            740                 745                 750

Leu Ser Tyr Gln Ser Ala Leu Ser Lys Asp Pro Asn Glu Lys Arg Asp
        755                 760                 765

His Met Val Leu Leu Glu Phe Val Thr Ala Ala Gly Ile Thr Leu Gly
        770                 775                 780

Met Asp Glu Leu Tyr Lys Leu Ala Ala Ala Leu Glu His His His His
785                 790                 795                 800

His His

<210> SEQ ID NO 38
<211> LENGTH: 767
<212> TYPE: PRT
<213> ORGANISM: Artificial
<220> FEATURE:
<223> OTHER INFORMATION: CrbsBY-ND
```

<400> SEQUENCE: 38

```
Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Asn
225                 230                 235                 240

Asp Met Lys Asp Thr Ile Ala Leu Val Val Ser Thr Leu Asn Asn Pro
                245                 250                 255

Phe Phe Val Ser Leu Lys Asp Gly Ala Gln Lys Glu Ala Asp Lys Leu
            260                 265                 270

Gly Tyr Asn Leu Val Val Leu Asp Ser Gln Asn Asn Pro Ala Lys Glu
        275                 280                 285

Leu Ala Asn Val Gln Asp Leu Thr Val Arg Gly Thr Lys Ile Leu Leu
    290                 295                 300

Ile Asn Pro Thr Asp Ser Asp Ala Val Gly Asn Ala Val Lys Met Ala
305                 310                 315                 320

Asn Gln Ala Asn Ile Pro Val Ile Thr Leu Asp Arg Gln Ala Thr Lys
                325                 330                 335

Gly Glu Val Val Ser His Ile Ala Ser Asp Asn Val Leu Gly Gly Lys
            340                 345                 350

Ile Ala Gly Asp Tyr Ile Ala Lys Lys Ala Gly Glu Gly Ala Lys Val
        355                 360                 365

Ile Glu Leu Gln Gly Ile Ala Gly Thr Ser Ala Ala Arg Glu Arg Gly
    370                 375                 380

Glu Gly Phe Gln Gln Ala Val Ala Ala His Lys Phe Asn Val Leu Ala
385                 390                 395                 400
```

-continued

```
Ser Gln Pro Ala Asp Phe Asp Arg Ile Lys Gly Leu Asn Val Met Gln
            405                 410                 415

Asn Leu Leu Thr Ala His Pro Asp Val Gln Ala Val Phe Ala Gln Asn
        420                 425                 430

Asp Glu Met Ala Leu Gly Ala Leu Arg Ala Leu Gln Thr Ala Gly Lys
    435                 440                 445

Ser Asp Val Met Val Val Gly Phe Asp Gly Thr Pro Asp Gly Glu Lys
450                 455                 460

Ala Val Asn Asp Gly Lys Leu Ala Ala Thr Ile Ala Gln Leu Pro Asp
465                 470                 475                 480

Gln Ile Gly Ala Lys Gly Val Glu Thr Ala Asp Lys Val Leu Lys Gly
                485                 490                 495

Glu Lys Val Gln Ala Lys Tyr Pro Val Asp Leu Lys Leu Val Val Lys
            500                 505                 510

Gln Ser Gly Ser Met Val Ser Lys Gly Glu Leu Phe Thr Gly Val
        515                 520                 525

Val Pro Ile Leu Val Glu Leu Asp Gly Asp Val Asn Gly His Lys Phe
    530                 535                 540

Ser Val Ser Gly Glu Gly Glu Gly Asp Ala Thr Tyr Gly Lys Leu Thr
545                 550                 555                 560

Leu Lys Phe Ile Cys Thr Thr Gly Lys Leu Pro Val Pro Trp Pro Thr
                565                 570                 575

Leu Val Thr Thr Phe Gly Tyr Gly Leu Gln Cys Phe Ala Arg Tyr Pro
            580                 585                 590

Asp His Met Lys Gln His Asp Phe Phe Lys Ser Ala Met Pro Glu Gly
        595                 600                 605

Tyr Val Gln Glu Arg Thr Ile Phe Phe Lys Asp Asp Gly Asn Tyr Lys
    610                 615                 620

Thr Arg Ala Glu Val Lys Phe Glu Gly Asp Thr Leu Val Asn Arg Ile
625                 630                 635                 640

Glu Leu Lys Gly Ile Asp Phe Lys Glu Asp Gly Asn Ile Leu Gly His
                645                 650                 655

Lys Leu Glu Tyr Asn Tyr Asn Ser His Asn Val Tyr Ile Met Ala Asp
            660                 665                 670

Lys Gln Lys Asn Gly Ile Lys Val Asn Phe Lys Ile Arg His Asn Ile
        675                 680                 685

Glu Asp Gly Ser Val Gln Leu Ala Asp His Tyr Gln Gln Asn Thr Pro
    690                 695                 700

Ile Gly Asp Gly Pro Val Leu Leu Pro Asp Asn His Tyr Leu Ser Tyr
705                 710                 715                 720

Gln Ser Ala Leu Ser Lys Asp Pro Asn Glu Lys Arg Asp His Met Val
                725                 730                 735

Leu Leu Glu Phe Val Thr Ala Ala Gly Ile Thr Leu Gly Met Asp Glu
            740                 745                 750

Leu Tyr Lys Leu Ala Ala Ala Leu Glu His His His His His His
        755                 760                 765
```

<210> SEQ ID NO 39
<211> LENGTH: 865
<212> TYPE: PRT
<213> ORGANISM: Artificial
<220> FEATURE:
<223> OTHER INFORMATION: CSY-LH

<400> SEQUENCE: 39

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Leu
225                 230                 235                 240

His Met Lys Ile Glu Glu Gly Lys Leu Val Ile Trp Ile Asn Gly Leu
                245                 250                 255

Phe Gly Tyr Asn Gly Leu Ala Glu Val Gly Lys Lys Phe Glu Lys Asp
            260                 265                 270

Thr Gly Ile Lys Val Thr Val Glu His Pro Asp Lys Leu Glu Glu Lys
        275                 280                 285

Phe Pro Gln Val Ala Ala Thr Gly Asp Gly Pro Asp Ile Ile Phe Tyr
    290                 295                 300

Ala His Asp Arg Phe Gly Gly Tyr Ala Gln Ser Gly Leu Leu Ala Glu
305                 310                 315                 320

Ile Thr Pro Asp Lys Ala Phe Gln Asp Lys Leu Tyr Pro Phe Thr Trp
                325                 330                 335

Asp Ala Val Arg Tyr Asn Gly Lys Leu Ile Ala Tyr Pro Ile Ala Val
            340                 345                 350

Tyr Ala Leu Ser Leu Ile Tyr Asn Lys Asp Leu Leu Pro Asn Pro Pro
        355                 360                 365

Lys Thr Trp Glu Glu Ile Pro Ala Leu Asp Lys Glu Leu Lys Ala Lys
    370                 375                 380

Gly Lys Ser Ala Leu Met Phe Asn Leu Gln Glu Pro Tyr Phe Thr Trp
385                 390                 395                 400

Pro Leu Ile Ala Ala Asp Gly Gly Tyr Ala Phe Lys Tyr Glu Asn Gly
            405                 410                 415
```

```
Lys Tyr Asp Ile Lys Asp Val Gly Val Asp Asn Ala Gly Ala Lys Ala
                420                 425                 430
Gly Leu Thr Phe Leu Val Asp Leu Ile Lys Asn Lys His Met Asn Ala
                435                 440                 445
Asp Thr Asp Tyr Ser Ile Ala Glu Ala Ala Phe Asn Lys Gly Glu Thr
                450                 455                 460
Ala Met Thr Ile Asn Gly Pro Trp Ala Trp Ser Asn Ile Asp Thr Ser
465                 470                 475                 480
Lys Val Asn Tyr Gly Val Thr Val Leu Pro Thr Phe Lys Gly Gln Pro
                485                 490                 495
Ser Lys Pro Phe Val Gly Val Leu Ser Ala Gly Ile Asn Ala Ala Ser
                500                 505                 510
Pro Asn Lys Glu Leu Ala Lys Glu Phe Leu Glu Asn Tyr Leu Leu Thr
                515                 520                 525
Asp Glu Gly Leu Glu Ala Val Asn Lys Asp Lys Pro Leu Gly Ala Val
                530                 535                 540
Ala Leu Lys Ser Tyr Glu Glu Glu Leu Ala Lys Asp Pro Arg Ile Ala
545                 550                 555                 560
Ala Thr Met Glu Asn Ala Gln Lys Gly Glu Ile Met Pro Asn Ile Pro
                565                 570                 575
Gln Met Ser Ala Phe Trp Tyr Ala Val Arg Thr Ala Val Ile Asn Ala
                580                 585                 590
Ala Ser Gly Arg Gln Thr Val Asp Glu Ala Leu Lys Asp Ala Gln Thr
                595                 600                 605
Asn Ser Ser Ser Gly Ser Met Val Ser Lys Gly Glu Glu Leu Phe Thr
                610                 615                 620
Gly Val Val Pro Ile Leu Val Glu Leu Asp Gly Asp Val Asn Gly His
625                 630                 635                 640
Lys Phe Ser Val Ser Gly Glu Gly Glu Gly Asp Ala Thr Tyr Gly Lys
                645                 650                 655
Leu Thr Leu Lys Phe Ile Cys Thr Thr Gly Lys Leu Pro Val Pro Trp
                660                 665                 670
Pro Thr Leu Val Thr Thr Phe Gly Tyr Gly Leu Gln Cys Phe Ala Arg
                675                 680                 685
Tyr Pro Asp His Met Lys Gln His Asp Phe Phe Lys Ser Ala Met Pro
                690                 695                 700
Glu Gly Tyr Val Gln Glu Arg Thr Ile Phe Phe Lys Asp Asp Gly Asn
705                 710                 715                 720
Tyr Lys Thr Arg Ala Glu Val Lys Phe Glu Gly Asp Thr Leu Val Asn
                725                 730                 735
Arg Ile Glu Leu Lys Gly Ile Asp Phe Lys Glu Asp Gly Asn Ile Leu
                740                 745                 750
Gly His Lys Leu Glu Tyr Asn Tyr Asn Ser His Asn Val Tyr Ile Met
                755                 760                 765
Ala Asp Lys Gln Lys Asn Gly Ile Lys Val Asn Phe Lys Ile Arg His
                770                 775                 780
Asn Ile Glu Asp Gly Ser Val Gln Leu Ala Asp His Tyr Gln Gln Asn
785                 790                 795                 800
Thr Pro Ile Gly Asp Gly Pro Val Leu Leu Pro Asp Asn His Tyr Leu
                805                 810                 815
Ser Tyr Gln Ser Ala Leu Ser Lys Asp Pro Asn Glu Lys Arg Asp His
                820                 825                 830
```

-continued

```
Met Val Leu Leu Glu Phe Val Thr Ala Ala Gly Ile Thr Leu Gly Met
        835                 840                 845

Asp Glu Leu Tyr Lys Leu Ala Ala Ala Leu Glu His His His His
    850                 855                 860

His
865
```

FLUORESCENT INDICATOR PROTEINS

CROSS-REFERENCE TO RELATED APPLICATION

This application claims priority under 35 USC 119 of Korean Patent Application No. 10-2005-067353 filed Jul. 25, 2005.

BACKGROUND OF THE INVENTION

1. Field of the Invention

The present invention relates to a protein biosensor having an increased signal intensity to the concentration of sugars and the use thereof, and more particularly to a fluorescent indicator protein in which fluorescent proteins of different emission wavelength ranges are fused to both ends of a binding protein undergoing a conformational change due to binding of sugars, such that a change in the concentration of various sugars involved in intracellular metabolism can be detected using a change in emission intensities caused by FRET (fluorescence resonance energy transfer), as well as a method for detecting the concentration of sugars using said fluorescent indicator protein.

2. Background of the Related Art

Fluorescent indicator proteins that use the fluorescence resonance energy transfer (FRET) between an enhanced blue fluorescent protein (EBFP) and an enhanced green fluorescent protein (EGFP) or enhanced cyan fluorescent protein (ECFP) and enhanced yellow fluorescent protein (EYFP), which are genetic mutants of a wild-type green fluorescent protein (wtGFP) derived from jellyfish, initiated for measuring intracellular $Ca^{2+}$ concentrations with a fusion protein, named 'cameleon', consisting of EBFP and EGFP fused to calmodulin and M13 peptide interacting therewith, by R Y Tsien and his colleagues at the University of California, San Diego, in the year 1997 (Miyawaki, A. et al.,*Nature,* 388:882, 1997; WO 98/40477). Also, in the year 1997, Hellinga and his colleagues constructed a biosensor having excellent sensitivity in vitro by attaching a fluorescent dye to a maltose binding protein (MBP) which is one of periplasmic binding proteins (PBPs) of microorganisms undergoing a conformational change due to binding of ligands, and examples of application to a variety of PBPs have been recently reported (Marvin, J. S. et al., *PNAS,* 94:4366, 1997; Robert, M. et al., *Protein Science,* 11:2655, 2002).

On the basis of such studies, in the year 2002, Frommer and coworkers reported results obtained by quantitatively measuring the concentration of maltose in living yeast using a method comprising fusing ECFP and EYFP to both ends of MBP, stably expressing the proteins in living yeast and determining the change in the ratio of the emission intensity of EYFP and that of ECFP (FRET change) (Fehr, M. et al., *PNAS,* 99:9846, 2002; WO 03/025220). They also reported study results obtained by quantitatively analyzing each of substances in living cells using PBPs such as a ribose-binding protein (RBP), a glucose/galactose-binding protein (GGBP) and a glutamin-binding protein (GlnBP) (Lager, I. et al., *FEBS Lett.,* 553:85, 2003; Fehr, M. et al., *JBC.,* 278:19127, 2003; Okumoto, S. et al., *PNAS,* 102:8740, 2004). The 'cameleon' and its improved derivatives were applied to the monitoring of various substance concentrations in living cells. For example, they were applied to real-time observation of the concentration change of GTP/GDP which play an important role in intracellular signaling (Mochizuki, N. et al., *Nature,* 411:1065, 2001); measurement of neurotoxin activity of *C. botulinum* (Dong, M. et al., *PNAS,* 101:14701, 2004); and quantitative measurement of inositol 1,4,5-trisphosphate in living cells (Tanimura, A. et al., *JBC.,* 279:38095, 2004).

In relation to biosensors for environmental monitoring, new biosensors were developed by reconstructing RBP into a protein capable of binding to environmentally harmful substances, such as TNT, using a genetic manipulation method based on in silico protein design (Looger, L. L. et al., *Nature,* 423:185, 2003). Also, there was an successful example of reconstructing a novel binding protein in which sucrose can bind to the maltose binding site, which was based on a conformational modification of MBP by inserting β-lactamase into a specific site of MBP with a conformational change due to binding of maltose (Guntas, G. et al., *PNAS,* 102:11224, 2005). This can be considered as a basic technology which allows the development of a 'designable FRET sensor' having a novel binding protein introduced into a binding protein similar to said 'cameleon', and thus is useful for the analysis of various cellular functions.

However, because said fluorescent indicator proteins developed in the initial stage have a disadvantage of very weak sensitivity, there is a need to develop a fluorescent indicator protein having excellent sensitivity, which can be used as a means for more precise and quantitative measurement (Fehr, M. et al., *Current Opinion in Plant Biology,* 7:345, 2004). Also, there were recently attempts to overcome this disadvantage, and in one of such attempts, Miyawaki and his research team have continuously presented study results suggesting that poor signal intensity of fluorescent indicator protein can be increased by circularly permuting the EYFP gene of 'cameleon' (Nagai, T. et al., *PNAS,* 98:3197, 2001; Nagai, T. et al., *PNAS,* 101:10554, 2004; WO 05/036178). Also, Frommer and coworkers presented study results suggesting that the FRET signal change of each of fluorescent indicator proteins can be greatly increased using an in-frame fusion of inserting a fluorescent protein into genes such as GGBP or GlnBP (Deuschle, K. et al., *Protein Science,* 14:2304, 2005). However, in order to apply said methods to increase the signal intensity of fluorescent indicator proteins, there are problems in that a high degree of technology is required for genetic manipulation and all development processes should be redesigned at the starting with the initial stage for the construction of novel fluorescent indicator proteins consisting of binding proteins and fluorescent proteins which have different conformational and kinetic characteristics.

Accordingly, the present inventors have made extensive efforts to solve the above-described problems and, as a result, found that the construction of a fluorescent indicator protein having an increased signal intensity to various sugar concentration ranges is possible using a method of inserting a short random peptide between a binding protein and a fluorescent protein or genetically mutating a specific site of a binding protein, to which a substance is to be bound, and then subjecting the resulting fluorescent indicator proteins to high-throughput screening, thereby completing the present invention.

SUMMARY OF THE INVENTION

One aspect of the present invention relates to a fluorescent indicator protein having an excellent signal intensity to the concentration of sugars, as well as a method for detecting a change in the concentration of sugars in microorganisms using said fluorescent indicator protein.

Another aspect of the present invention relates to a nucleic acid encoding said fluorescent indicator protein, as well as, recombinant microorganisms transformed with a recombinant expression vector containing said nucleic acid. Still another aspect of the present invention relates to a method for preparing a fluorescent indicator protein having an increased signal intensity to the concentration of sugars, the method comprising culturing said recombinant microorganisms.

The above and other objects, features and embodiments of the present invention will be more clearly understood from the following detailed description and the accompanying claims.

BRIEF DESCRIPTION OF THE DRAWINGS

FIG. 8 is a graphic diagram showing the comparison of binding affinity to various sugars between the inventive MBP fusion proteins having different quantitative characteristics.

FIG. 10 shows results by observing a change in the concentration of maltose in living yeast cells by FRET imaging using a fluorescence microscope, in which

FIG. 11 is a graphic diagram of Sigmoidal curves expressing changes in FRET efficiency according to changes of allose, arabinose and ribose concentrations for each of fusion proteins constructed by introducing ALBP, ARBP and RBP into a sensing portion.

FIG. 12 is a graphic diagram showing the comparison of binding affinity to various sugars between fusion proteins constructed by introducing each of ALBP, ARBP and RBP into the sensing portion.

FIG. 13 is a graphic diagram of Sigmoidal curves expressing changes in ⊿ratio according to changes of sucrose and maltose concentrations for SBP (sucrose-binding protein) fusion proteins in which SBP reconstructed by genetic mutation of MBP is introduced as the binding moiety.

DETAILED DESCRIPTION OF THE INVENTION, AND PREFERRED EMBODIMENT

Figure 1:
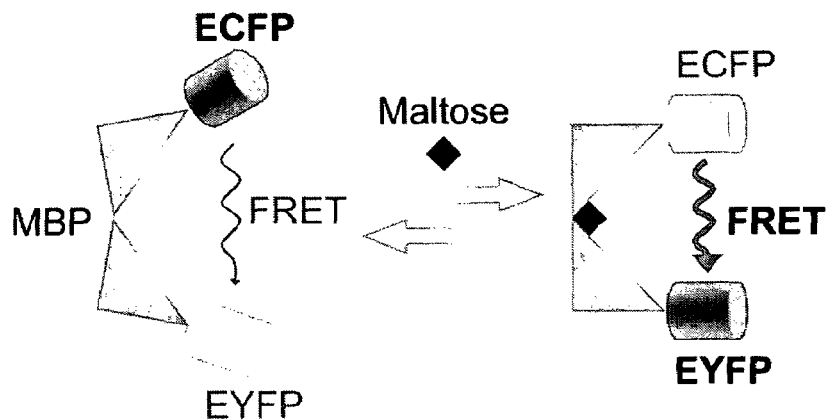
FIG. 1 shows the basic construction and operational principle of MBP fusion protein as an example of a fluorescent indicator protein according to the present invention.

The present invention provides a fluorescent indicator protein having an increased signal intensity to the concentration of sugars, which is represented by Formula I:

[Formula I]

wherein, BP (binding protein) is selected from the group consisting of MBP (maltose binding protein), ALBP (allose binding protein), ARBP(arabinose binding protein), RBP (ribose binding protein) and SBP (sucrose binding protein); $L_1$ and $L_2$ consist of two amino acids or short peptides; $FP_1$ is selected from the group consisting of ECFP (enhanced cyan fluorescent protein), EBFP (enhanced blue fluorescent protein) and EGFP (enhanced green fluorescent protein), and $FP_2$ is selected from the group consisting of EYFP (enhanced yellow fluorescent protein), EGFP (enhanced green fluorescent protein) and RFP (red fluorescent protein).

In the present invention, preferably, said BP is MBP, and said $L_1$ is Gln-Ile or Leu-His. In this case, said fluorescent indicator protein (MBP fusion protein) has an amino acid sequence set forth in SEQ ID NO: 31 or SEQ ID NO: 32.

Preferably, said BP is ALBP, and $L_1$ is Gln-Val. In this case, said fluorescent indicator protein (ALBP fusion protein) has an amino acid sequence set forth in SEQ ID NO: 36.

Preferably, said BP is ARBP, and $L_1$ is Pro-Arg. In this case, said fluorescent indicator protein (ARBP fusion protein) has an amino acid sequence set forth in SEQ ID NO: 37.

Preferably, said BP is RBP, and $L_1$ is Asn-Asp. In this case, said fluorescent indicator protein (RBP fusion protein) has an amino acid sequence set forth in SEQ ID NO: 38.

Preferably, said BP is a MBP mutant which has a mutation at position 62 in the amino acid sequence of SEQ ID NO: 30.

Preferably, said mutation is selected from a group consisting of Trp62Ala, Trp62His and Trp62Leu. In this case, said fluorescent indicator protein has an amino acid sequence selected from the group consisting of SEQ ID NO: 33 to 35.

Preferably, said BP is SBP, and said SBP is a mutant of MBP has an amino acid sequence set forth in SEQ ID NO: 30. Preferably, said mutant comprises at least mutations of Asp14Leu, Lys15Phe, Trp62Tyr, Glu111Tyr in the amino acid sequence set forth in SEQ ID NO: 30. In this case, said fluorescent indicator protein (SBP fusion protein) preferably has an amino acid sequence set forth in SEQ ID NO: 39.

In another aspect, the present invention provides a nucleic acid encoding said fluorescent indicator protein. In addition, the present invention provides a recombinant vector containing said nucleic acid. Preferably, said recombinant vector is selected from the group consisting of pECMY-QI, pECMY-LH, pECSY-LH, pECMY-LH/W62A, pECMY-LH/W62H and pECMY-LH/W62L. Preferably, said recombinant vector may additionally contain a targeting signal sequence. Also, said recombinant vector may additionally contain a targeting signal sequence and an anchoring sequence.

In still another aspect, the present invention provides a recombinant microorganism or cell obtained by introducing the recombinant vector containing said nucleic acid into a host cell selected from the group consisting of bacteria, yeasts, fungi, and animal and plant cells.

In yet another aspect, the present invention provides a method for preparing the fluorescent indicator protein of Formula I, the method comprising the steps of: (a) culturing said recombinant microorganism or cell to express said fluorescent indicator protein therein; and (b) collecting said fluorescent indicator protein from the cultured microorganism or cell.

In another further aspect, the present invention provides a method for detecting a change in the concentration of sugars in microorganisms and cells using the fluorescent indicator protein of Formula I, the method comprising the steps of: (a) culturing said recombinant microorganism or cell to express the fluorescent indicator protein of Formula I therein; and (b) analyzing a change in the concentration of sugars in the cultured microorganism or cell using a fluorescence analysis system.

In the present invention, the step (b) preferably comprises analyzing the concentration of sugars in microorganism or cell by comparing a change in the fluorescent intensity ratio between a fluorescent donor and a fluorescent acceptor using a fluorescent analysis system. In the present invention, the fluorescence analysis system is preferably a confocal microscope or a fluorescence microscope.

Among said BPs, SBP (sucrose binding protein) may be a protein redesigned from MBP (Guntas, G. et al., *PNAS*, 102: 11224, 2005). As said SBP, any protein may be used as long as it can specifically bind to a substance to be sensed and undergoes a conformational change due to binding of the substance to be detected.

Said $FP_1$ and $FP_2$ are the fluorescent donor and acceptor which are used as signal generation portions. As $FP_1$ and $FP_2$, any substances may be used as long as they can induce FRET by the overlapping of the emission spectrum of the donor and the absorption spectrum of the acceptor. Among these substances, ECFP and EYFP are preferably used in view of possible expression as monomers, the extinction coefficient, quantum efficiency and photostability of expressed fluorescent proteins, and the like. The operational principle of said fluorescent indicator protein is shown in FIG. 1.

Hereinafter, the present invention will be described in further detail.

The present invention relates to a protein biosensor capable of quantitatively measuring the concentration of substances which are absorbed or metabolized in vitro or in vivo. The inventive biosensor is a fluorescent indicator protein in which a binding protein that undergoes a change in the three-dimensional conformation thereof due to binding of a substance to be sensed is fused between two different kinds of fluorescent proteins which can induce FRET therebetween. The fluorescent indicator protein can be used to quantitatively measure a substance to be detected, because the conformational change of the binding protein, resulting from binding of the substance to be detected, causes a change in FRET, and thus leads to a change in emission wavelengths, which is proportional to the concentration of the bound substance.

As used herein, the term "fluorescence resonance energy transfer (FRET)" refers to non-radiative energy transfer occurring between two different fluorescent substances, in which the excited-state energy of a donor is transferred to an acceptor. FRET is generally called 'resonance energy transfer', because a short wavelength emitted from the donor overlaps with the absorption spectrum of the acceptor and it occurs without the appearance of a photon. This results from the long-range dipole-dipole interaction between the donor and the acceptor. The energy transfer efficiency of FRET varies depending on the spectral overlap of the donor emission spectrum and the acceptor absorption spectrum, the quantum yield of the donor, the relative orientation of the transition dipoles of the donor and acceptor, and the distance between the donor and acceptor molecules. Thus, the energy transfer efficiency of FRET is influenced by the distance and relative orientation between the donor and acceptor molecules, and is expressed by the following Förster's equation as follows:

$$E = R_0^6/(R^6 + R_0^6) \quad \text{[Equation 1]}$$

wherein E denotes the efficiency of FRET, R is the distance between the donor and the acceptor, and the distance at which FRET can occur is generally defined as 2-9 nm or shorter, even though it varies depending on fluorescent substances forming the donor and acceptor. Also, $R_0$ is the distance between the donor and the acceptor at which the efficiency of FRET is 50%, and $R_0$ is generally called "Förster distance" or "Förster radius". $R_0$ is expressed by the following equation:

$$R_0 = 0.211[k^2 n^{-4} Q_D J(\lambda)]^{1/6} (\text{in Å}) \quad \text{[Equation 2]}$$

wherein $k^2$ is an orientation factor, which is often assumed to be 2/3, and has a value of 0-4 depending on the relative orientation of the donor emission and the acceptor absorption. N is the refractive index of a medium and is generally ~1.334 for water at 25° C., and $Q_D$ is the quantum yield of the donor. $J(\lambda)$ is the degree of spectral overlap of the donor emission spectrum and the acceptor absorption spectrum and is expressed in a unit of $M^{-1} cm^{-1} nm^4$ (Lakowicz, J. R., *Principles of Fluorescence Spectroscopy*, 2nd ed., New York: Plenum Press, 1999; Patterson, G. H. et al., *Anal. Biochem.*, 284:438, 2000; Patterson, G. H. et al., *J. Cell Sci.*, 114:837, 2001).

Using the above-described principle of FRET, the present inventors constructed a fluorescent indicator protein in which fluorescent proteins ECFP and EYFP acting as the donor and acceptor of FRET were fused to both ends of MBP. Such a fluorescent indicator protein (MBP fusion protein) was expressed in living cells to quantitatively measuring the concentration of maltose absorbed into the cells. More specifically, the present inventors constructed a MBP fusion protein using a method of screening a MBP fusion protein having excellent signal intensity by inserting a short random peptide between ECFP and MBP in order to change the distance and relative orientation between the donor and the acceptor which influence the energy transfer efficiency of FRET. Also, in the construction of the fluorescent indicator protein, specific sites of MBP to which maltose binds were genetically engineered such that the MBP fusion protein could detect maltose present at various concentrations.

Also, the present invention provides a method for improving and constructing a fluorescent indicator protein (MBP fusion protein), comprising the steps of: (1) either constructing a library in which the base sequence of a fusion site between a MBP gene and an ECFP gene in a fusion protein consisting of ECFP-MBP-EYFP is varied, or constructing a MBP fusion protein expression vector library after genetically engineering a specific site of MBP to which maltose binds; (2) performing high-throughput screening of MBP fusion proteins showing an increase in signal intensity and a change in quantitative characteristics, from E. coli transformed with the MBP fusion protein expression vector library, and analyzing the screened proteins; (3) quantitatively measuring the concentration of maltose absorbed into a single cell using the above-screened MBP fusion protein showing an increase in signal intensity; and (4) applying the above development method to other kinds of binding proteins having a conformation and function similar to those of MBP so as to construct a fluorescent indicator proteins for detecting new substances.

The MBP fusion protein according to the present invention is one polypeptide consisting of ECFP-MBP-EYFP as shown in FIG. 1 and is expressed as a large fusion protein chimera. In the inventive MBP fusion protein, considering that the size of MBP is about 3×4×6.5 nm (Spurlino, J. C. et al., *J. Biol. Chem.*, 266:5202, 1991), ECFP and EYFP are located at a distance of about 5-6 nm, at which FRET can occur. Thus, when ECFP is excited at 436 nm, the excited-state energy of ECFP is transferred to EYFP, such that ECFP and EYFP emissions can be simultaneously observed. When maltose binds to this MBP fusion protein, the distance and relative orientation between ECFP and EYFP fused to both ends of MBP are changed, and it is possible to detect maltose by measuring a change in the emission intensity ratio between the two fluorescent proteins, which results from a change in the efficiency of FRET between ECFP and EYFP. The change in the emission intensity ratio can be quantitatively measured, because it is proportional to the concentration of maltose.

In addition, the FRET pair of ECFP and EYFP has an $R_0$ value of about 5 nm as calculated according to said Equation 2 (Patterson, G. H. et al., *Anal. Biochem.*, 284:438, 2000), and thus, if the distance between CFP and YFP is assumed to be about 5-6 nm, a small change in the distance or relative orientation therebetween can make a great difference in the efficiency of FRET. Thus, if it is possible to minimize the efficiency of FRET before binding of maltose and to maximize the FRET efficiency resulting from binding of maltose, the signal intensity of the MBP fusion protein will be greatly increased. It can be expected that this regulation of the FRET efficiency is possible by changing the structure of a fusion site between MBP and the two fluorescent proteins so as to change the distance and relative orientation between ECFP and EYFP.

Figure 2A:
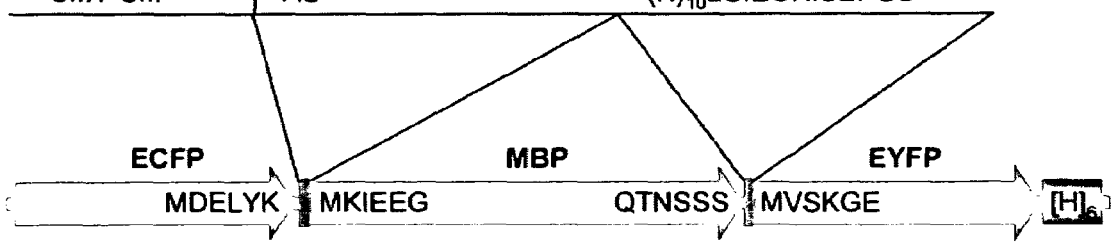
FIG. 2A is a schematic diagram showing the inventive MBP fusion proteins having a difference at both ends of MBP connected with fluorescent proteins.
Figure 2B:
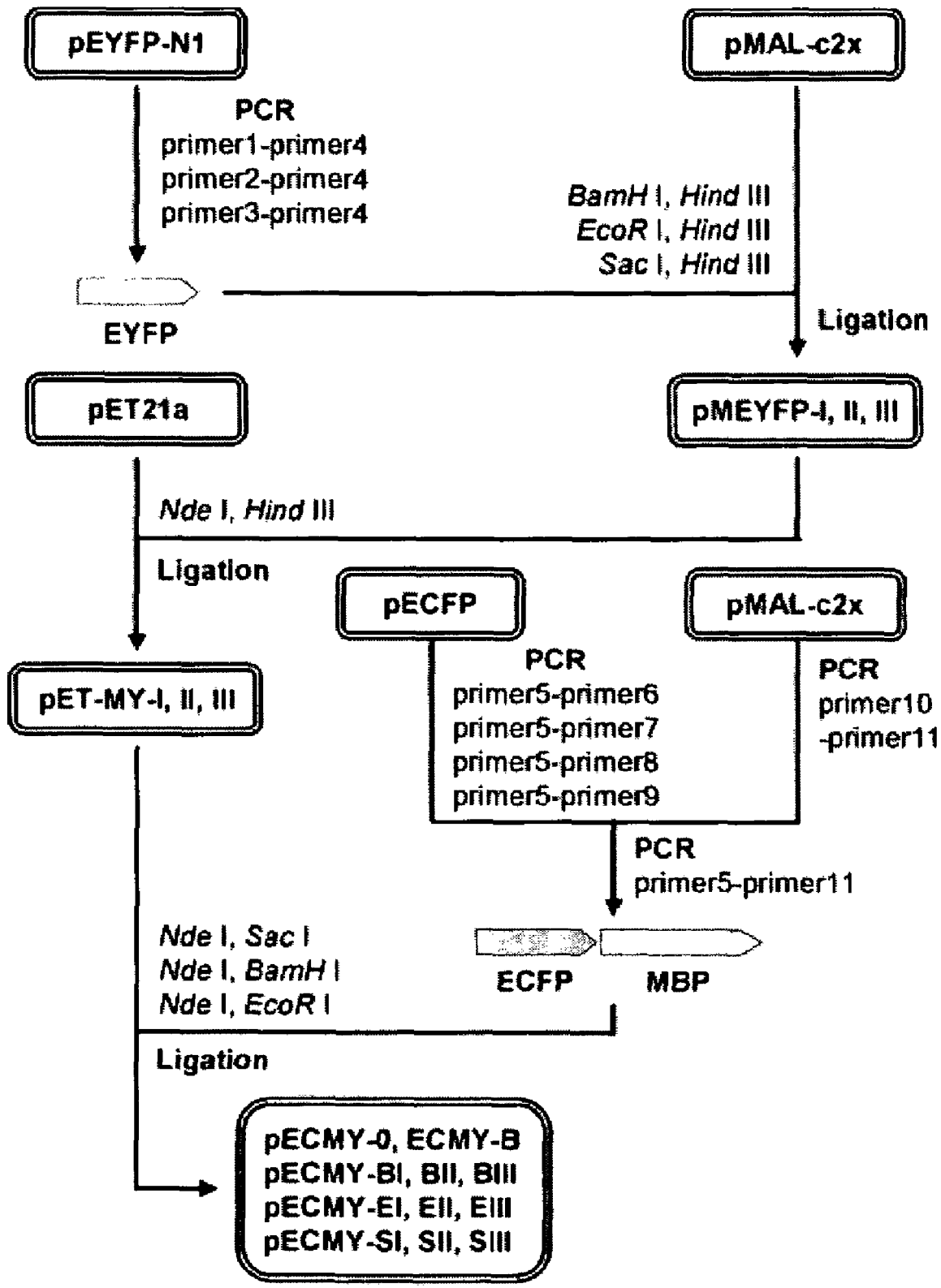
FIG. 2B is a flow diagram showing a process for constructing expression vectors for expressing said MBP fusion proteins.

Thus, in a study conducted by the present inventors, each of 11 kinds of genes, which were designed such that connecting peptides having various compositions and lengths were inserted into both ends of MBP as shown in FIG. 2A, was inserted into a restriction enzyme site present between the T7 promoter of expression vector pET21a(+) (Novagen, Germany) and the base sequence of His-6 tag, thus constructing MBP fusion protein expression vectors depicted in FIG. 2B. For expression and purification for in vitro experiments, the MBP fusion protein expression vectors were transformed into host *E. coli* JM109 (DE3) (Promega, USA) having a T7 RNA polymerase gene in the chromosome, and the transformed *E. coli* were cultured in LB media, while inducing the expression of the MBP fusion proteins by the addition of IPTG (isopropyl-β-d-thiogalactopyranoside). Each of the MBP fusion proteins was bound to a HisTrap™ HP1 column (Amersham Biosciences, Sweden) packed with Ni Sepharose™, using His-6 tag expressed at the ends thereof, and then purified by gradient elution using imidazole.

The above-purified eleven kinds of MBP fusion proteins were validated for fluorescent characteristics required in MBP fusion proteins in the following manner. One of important requirements for use as MBP fusion proteins is that the fluorescent proteins fused to both ends of MBP should not interfere with the binding of maltose to MBP. Thus, a fusion protein having EYFP fused to the end of MBP, and said 11 kinds of MBP fusion proteins, were subjected to a pull-down assay using amylose resin (NEB, USA) in the following manner in order to examine whether maltose was bound to MBP of said MBP fusion proteins.

Figure 3:
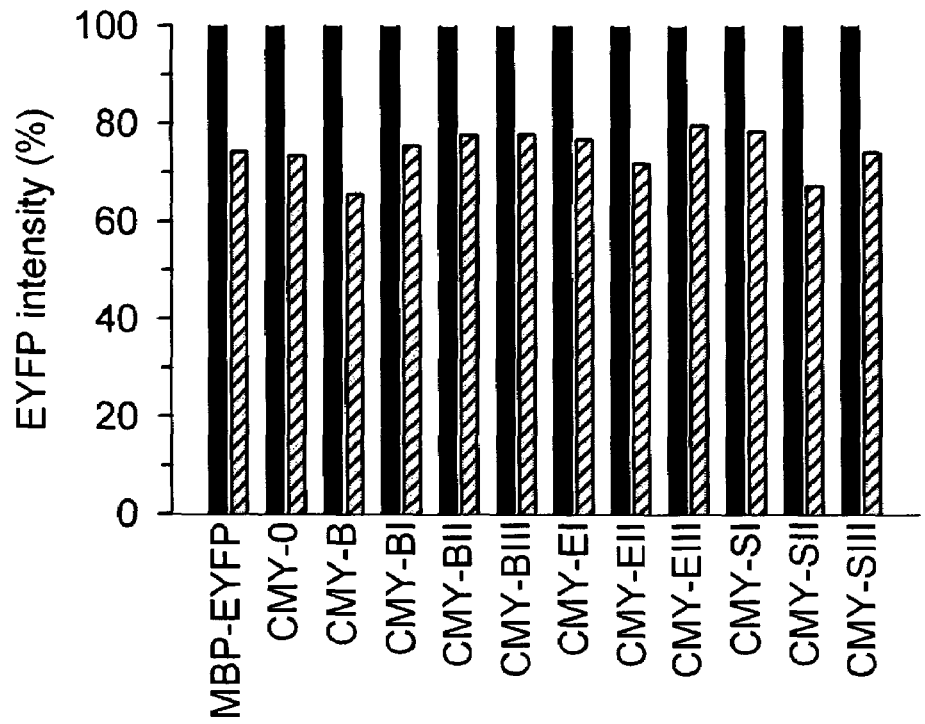
FIG. 3 shows whether MBP fusion proteins expressed from vectors constructed in Example 1 bind to amylose resin (the binding ability of fusion proteins) (■: emission intensity of EYFP before pulling-down with amylose resin; and ▨: emission intensity of EYFP in a supernatant after pulling down with amylose resin).

Each of the MBP-EYFP fusion protein and said 11 kinds of MBP fusion proteins was mixed with amylose resin and precipitated by centrifugation. Then, the emission intensity of EYFP remaining in each of the supernatants was measured at a wavelength of 510 nm and compared with the emission intensity of EYFP before binding to amylose resin, thereby analyzing whether maltose was bound to MBP. As shown in FIG. 3, the emission intensities of the remaining EYFP of the MBP-EYFP fusion protein and said 11 kinds of MBP fusion proteins were about 70% compared to the emission intensities of EYFP before binding to amylose resin, which were similar to each other. Accordingly, it was considered that ECFP and EYFP fused to both ends of MBP do not influence the bonding of maltose to MBP.

Figure 4:
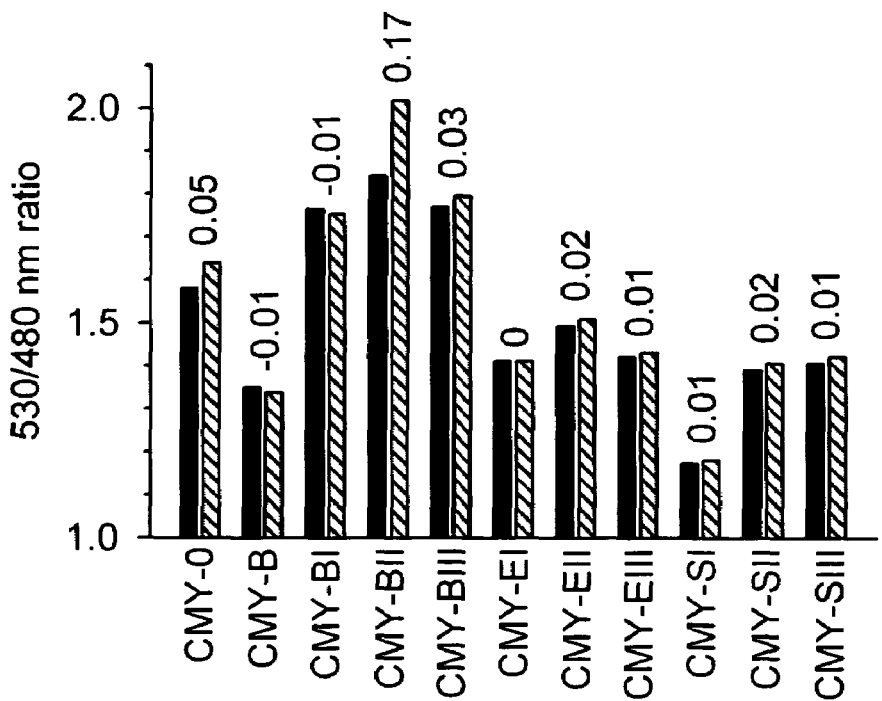
FIG. 4 shows the comparison of a change in FRET efficiency caused by binding of maltose between MBP fusion proteins expressed from vectors constructed in Example 1 (■: FRET efficiency before binding to maltose; ▨: FRET efficiency after binding to maltose; and numerical numbers above bars: ⊿ratio indicative of signal intensity).

Then, said 11 kinds of MBP fusion proteins were analyzed for the efficiency of FRET according to the method described in Example 3 in detail. The FRET efficiency was analyzed at the peak emission ratio between EYFP and ECFP (530 nm/480 nm) in a spectrum observed when exciting ECFP at a wavelength of 436 nm. As shown in FIG. 4, the analysis results varied depending on the lengths and compositions of the peptides connecting the fluorescent proteins to MBP.

As a result, it was found that the FRET efficiency of the MBP fusion proteins varies depending on the lengths and compositions of the peptides connecting the fluorescent proteins to MBP, and this difference in the lengths and compositions of the peptides also greatly influences a signal intensity (Δratio) of the MBP fusion proteins, which results from binding of maltose.

The present inventors constructed a MBP fusion protein expression vector library which was subjected to saturation mutagenesis with mutation primers, such that six base sequences connecting the ECFP gene of pECMY-BII (CMY-BII expression vector) to the MBP gene could be substituted with various combinations. In the present invention, although various combinations of connecting peptides each consisting of two amino acids were produced between ECFP and MBP by substituting six optional base sequences into reverse primers used in the amplification of the ECFP gene, it is also possible to construct a library in which various combinations of connecting peptides are also produced at the C-terminal end of MBP.

The MBP fusion protein expression vector library constructed according to the above-described method was transformed into *E. coli* JM109 (DE3), and then about 4,000 fusion proteins were investigated by analyzing a change in the $\Delta$ratio of the individual MBP fusion proteins to maltose using a microtiter fluorometer. Thus, MBP fusion proteins showing a great increase in signal intensity, i.e., MBP fusion protein CMY-QI of SEQ ID NO: 31 and MBP fusion protein CMY-LH of SEQ ID NO: 32, were selected.

Meanwhile, as disclosed in a previously published document, when the Trp62 of MBP is substituted with Ala, the $K_d$ of MBP and the quantification range for maltose can be changed (Martineau, P. et al., *J. Mol. Biol.,* 214:337, 1990). Thus, a MBP fusion protein expression vector library showing a change in the binding ability to maltose was constructed by performing genetic manipulation for substituting the Trp62 of MBP with a variety of amino acids. In the present invention, although the Trp62 of MBP was substituted, the concept of this substitution can likewise be applied to the amino acids of binding sites reported to make a hydrogen bond or Van Der Waals interaction with maltose.

In the present invention, the MBP fusion protein expression vector library constructed according to the above method was transformed into *E. coli* JM109 (DE3) and then screened. As a result, MBP fusion proteins showing an increase in sensitivity and a change in quantitative characteristics, i.e., MBP fusion protein CMY-LH/W62A of SEQ ID NO: 33, MBP fusion protein CMY-LH/W62H of SEQ ID NO: 34 and MBP fusion protein CMY-LH/W62L of SEQ ID NO: 35, were secured.

An *E. coli* strain transformed with the expression vector CMY-LH/W62L in the present invention was deposited in the Korean Collection for Type Cultures (KCTC) (located at KRIBB #52, Oun-dong, Yusong-gu, Daejon 305-333, Republic of Korea), an international depository authority, on Jul. 14, 2005, and assigned accession No. KCTC 10830BP. However, the vectors used or constructed in the present invention do not necessarily need to be deposited, because these vectors can be constructed from commercially available vectors according to the methods described in Examples below in detail.

The fluorescent indicator proteins according to the present invention can be efficiently used in the field, in which the concentration of substances absorbed or metabolized in vivo is quantitatively measured and analyzed. In the present invention, the MBP fusion proteins having increased signal intensity were expressed in living yeast and analyzed by imaging. For example, the present inventors constructed recombinant expression vectors YEG-CMY-B, YEG-CMY-BII, YEG-CMY-LH and YEG-CMY-LH/W62L, in which genes allowing the expression of the MBP fusion proteins were inserted downstream of the GAL promoter of YEGα-HIR525 (Sohn et al., *Process Biochemistry,* 30:653, 1995). The above-constructed expression vectors of the MBP fusion proteins were transformed into auxotrophic strain *Saccharomyces cerevisiae* 2805 (Sohn et al., *Process Biochemistry,* 30:653, 1995), and the expression and imaging of the MBP fusion proteins in the transformed strain were analyzed using a fluorescence microscope.

The present invention is not limited only to the object of increasing the signal intensity of the fluorescent indicator protein to a specific substance, and can be widely applied for the development of a variety of fluorescent indicator proteins having increased signal intensity. For example, among binding proteins of BPs having a structure and function similar to those of MBP, it is possible to use ALBP, ARBP, RBP, SBP and the like in place of MBP.

In the present invention, in order to make fluorescent indicator proteins having new bonding ability using the above-constructed MBP fusion proteins, the gene of SBP (Guntas, G. et al., *PNAS,* 102:11224, 2005) prepared by partially mutating the previously known MBP gene was substituted into the MBP gene site of the MBP fusion protein expression vectors. Accordingly, the SBP gene made by partially mutating the MBP gene was constructed, and SBP fusion protein expression vectors were constructed by inserting and substituting the SBP gene into the MBP gene site of existing MBP fusion protein expression vectors, pECMY-B, pECMY-BII and pECMY-LH.

EXAMPLES

Hereinafter, the present invention will be described in detail with reference to examples. It is to be understood, however, that these examples are for illustrative purposes only and are not to be construed to limit the scope of the present invention.

Example 1

Construction of Recombinant Vectors for Expression of MBP Fusion Proteins

As shown in FIG. 2A, the fluorescent indicator proteins (MBP fusion proteins) for detection of maltose were constructed of three protein domains (ECFP, MBP, EYFP) and two composite linkers, which composed of connecting peptides (cc, yc) and unstructured terminal regions of flanking proteins: ECFP-cc-MBP-yc-EYFP. In order to construct vectors for the expression of the inventive fluorescence indicators, genes were amplified with primers of SEQ ID NOs: 1 to 11 and were used to construct the expression vectors.

First, to obtain the gene of EYFP, PCR was performed using a pEYFP-N1 vector (Clontech, USA) as a template with primers of SEQ ID NOs: 1 to 4, which were introduced with a SacI, EcoRI or BamHI restriction enzyme recognition site at the 5' end and a HindIII restriction enzyme site at the 3' end. The amplified EYFP gene was digested with SacI and EcoRI, or with BamHI and HindIII, and then inserted into each of the restriction enzyme sites of a pMALc2x vector (NEB, USA) which is an MBP expression vector so as to construct pMEYFP-I, pMEYFP-II, and pMEYFP-III. The three vectors were digested with NdeI and HindIII to obtain MBP-yc-EYFP genes, which were then introduced into corresponding site of a pET21a(+) (Novagen, Germany), thus constructing expression vectors of pET-MY-I, pET-MY-II and pET-MY-III.

Next, the genes for ECFP-cc-MBP were prepared by combining the ECFP gene of pECFP vector (Clonetech, USA) and the MBP gene of pMALc2x with different ECFP-side connectors (cc). The ECFP gene was amplified by one forward primer of SEQ ID NO:5 and four reverse primers of SEQ ID NO:6-9, which were consisted of the 3' end of ECFP, cc, and 5' end of MBP. The gene of MBP was obtained by performing PCR using a pMALc2x vector (NEB, USA) as a template with a primer of SEQ ID NO: 10 and a primer of SEQ ID NO: 11, which was introduced with both SacI and BamHI restriction enzyme recognition sites at the 3' end.

Because each of the ECFP and MBP genes thus amplified could be subjected to overlap-extension PCR using primers constructed so as to overlap with each other, a variety of genes, in which ECFP and MBP were synthesized and amplified, could be obtained by adding the same amounts of the ECFP and MBP genes to a reaction solution and then performing PCR using primers of SEQ ID NO: 5 and SEQ ID NO: 11. The amplified ECFP-MBP genes were digested with NdeI and SacI or BamHI restriction enzymes, and inserted into the restriction enzyme recognition sites of MBP-yc-EYFP expression vectors, pET-MY-I, pET-MY-II and pET-MY-III, thus constructing 11 kinds of fusion protein expression vectors, in which connecting peptides having various combinations and lengths could be produced at both ends of MBP. The constructed expression vectors were termed "pECMY series", and MBP fusion proteins expressed from said vectors were termed "CMY series" (FIGS. 2A and 2B).

Example 2

Expression and Purification of MBP Fusion Proteins (Fluorescent Indicator Proteins)

The MBP fusion protein expression vectors constructed in Example 1 were transformed into *E. Coli* JM109 (DE3) (Promega, USA), and the transformed recombinant strains were inoculated into LB media (1% bacto-trypton, 0.5% yeast extract, 1% NaCl) containing 50 µg/ml of ampicillin and 0.5 mM IPTG (isopropyl β-d-thiogalactoside), and were cultured with shaking at 28° C. for 24 hours to induce expression. The expressed *E. coli* were collected by centrifugation and suspended in 50 mM sodium phosphate buffer (pH 7.5). The bacterial cells were disrupted by ultrasonification, centrifuged and then used in a subsequent purification process.

The MBP fusion proteins were purified with a Histrap™ HP1 column (Amersham Bioscience, Sweden) connected to FPLC (Fast Performance Liquid Chromatography, Amersham Biosciences, Sweden), using His-6 tag expressed at the C-terminus of EYFP. Buffer used in the purification process was 50 mM sodium phosphate buffer (pH 7.5) containing 0.5 mM PMSF (phenylmethylsulphonylfluoride), 1 mM DTT (dithiothreitol) and 20 mM imidazole. The proteins bound to the column were subjected to gradient elution with 50 mM sodium phosphate buffer containing 0.5 M imidazole. The purified MBP fusion proteins were eluted with 20% glycerol-containing PBS buffer (pH 7.4) in a Hitrap™ desalting column (Amersham Biosciences, Sweden) connected to the FPLC so as to exchange the buffer. The resulting fusion proteins were concentrated with 20 ml VIVASPIN (10,000 MWCO, Vivascience, Germany) and stored in a freezer at −80° C.

Example 3

Analysis of Fluorescence of MBP Fusion Proteins

The fluorescence analysis of the MBP fusion proteins expressed and purified in Example 2 was performed using fluorescence spectrophotometer Cary Eclipse (Varian, Australia) at 25° C., and the MBP fusion proteins were diluted in PBS buffer (pH 7.4) to the same concentrations of 0.2 µM. To define the FRET efficiency in the fluorescence analysis, the emission intensity ratio between the emission intensity of ECFP at 480 nm, measured at an excitation wavelength of 436 nm, and the emission intensity of EYFP at 530 nm, caused by FRET, was substituted into Equation 3 below for convenience:

Ratio=[530 nm/480 nm]     [Equation 3]

Also, an index of the signal intensity of fluorescence indicators was defined as the change of ratio ($\Delta$ratio) between the FRET efficiency (ratio$_{10\ mM}$) in the presence of 10 mM maltose and the FRET efficiency (ratio$_{apo}$) in the absence of maltose.

As shown in FIG. 4, the FRET efficiencies of MBP fusion proteins varied depending on the lengths and compositions of peptides connecting the fluorescent proteins to MBP. For example, the fusion proteins of the CMY-B series, which had a short connecting peptide of GS between MBP and EYFP, all showed a relatively high initial FRET efficiency (ratio$_{apo}$) of ~1.8, except for CMY-B (~1.3). On the other hand, the fusion proteins of the CMY-E and CMY-S series, in which MBP and EYFP connected to each other by a peptide consisting of more than 20 amino acids, showed a relatively low initial FRET efficiency (ratio$_{apo}$) between 1.2 and 1.5.

Also, on the basis of the FRET efficiency of the above-constructed 11 kinds of MBP fusion proteins, the signal intensity of the fusion proteins to maltose was measured. An index of the signal intensity to maltose was determined by $\Delta$ratio while referring to the previously reported document (Fehr, M. et al., *PNAS*, 99:9846, 2002). As a control group, CMY-0 ($\Delta$ratio=0.05) without having connecting peptide between MBP and fluorescent proteins was used. As shown in FIG. 4, the CMY-BII and CMY-BIII fusion proteins were shown to be most similar to each other except the ECFP-side connector (FIG. 2A), but the $\Delta$ratio of the CMY-BII was about six times as high as that of CMY-BIII. Also, among said 11 kinds of MBP fusion proteins, the CMY-BII having an SR connecting peptide between ECFP and MBP showed the highest $\Delta$ratio of 0.17. On the other hand, the fusion proteins of the CMY-E and CMY-S series showed very low $\Delta$ratio values regardless of the kind of a connecting peptide between ECFP and MBP, and this indicates that there is little or no difference between the FRET efficiency before binding to maltose, and the FRET efficiency caused by binding of maltose. From said results, it was considered that the connecting peptide between ECFP and MBP plays a very important role in $\Delta$ratio caused by binding of maltose. For this reason, the connecting peptide between ECFP and MBP was optimized in order to maximize $\Delta$ratio caused by binding of maltose.

Profiles of the ratios at wide substrate concentrations were fit by a four-parameter Hill equation with SigmaPlot (SSI, USA) and the binding substance concentration corresponding to the medium between ratio$_{10\ mM}$ and ratio$_{apo}$ was determined to be the dissociation constant (K$_d$) of the fusion proteins.

Meanwhile, as shown in Table 1, it was found that the $\Delta$ratio of CMY-BII, the quantitatively measurable concentration range of maltose, and the dissociation constant (K$_d$) of the fusion proteins, were similar to those of FLIPmal-2 µ (FLIPmal-5AA), which is a previously reported FRET-based nanosensor (Fehr, M. et al., *PNAS*, 99:9846, 2002; WO 03/025220).

Example 4

Construction of MBP Fusion Protein Library and Screening of Fluorescent Indicator Proteins On the basis of pECMY-BII which is a expression vector of CMY-BII, the MBP fusion protein expression vector library was constructed using mutating primer, such that a peptide of GS was inserted between MBP and EYFP, and various combinations of connecting peptides each consisting of two amino acids could be inserted between ECFP and MBP.

Specifically, the ECFP gene was amplified using primers of SEQ ID NO: 5 and SEQ ID NO: 12, and the MBP gene was amplified using primers of SEQ ID NO: 10 and SEQ ID NO: 11. The ECFP and MBP genes were synthesized and amplified by overlap-extension PCR using primers of SEQ ID NO; 5 and SEQ ID NO: 11, and the previously constructed pECMY-BII expression vector was digested with NdeI and BamHI restriction enzymes to remove the ECFP-MBP gene therefrom. Then, the amplified ECFP-cc-MBP genes were inserted into the vector, thus constructing the expression vector library. Thus, due to six N bases inserted between the ECFP and MBP genes, various peptides having the ECFP and MBP genes connected to each other by combinations of two amino acids could be produced, and the number of the produced peptides is assumed to be $4^6=4,096$, considering said six bases.

The above-constructed expression vector library of MBP fusion proteins was transformed into E. coli JM109 (DE3) (Promega, USA), and each of the resulting clones was inoculated onto a 96 deep-well plate (Bioneer, Korea) loaded with LB medium containing 50 μg/ml of ampicillin and 0.5 mM IPTG and was cultured for expression with shaking at 28° C. for 24 hours. The expressed E. coli were collected by centrifugation at 3,000×g for 20 minutes, and then dispersed in 250 μl of PBS buffer (pH 7.4) containing 1 unit of DNase, 20 μg/ml of lysozyme and 50% microbial cell lysate Cellytic B (Sigma, USA) for 1 hour so as to disrupt the cell membrane. The disrupted cells were centrifuged again at 3,000×g for 20 minutes, and 200 μl of the supernatant was transferred and analyzed in a new 96-well plate.

The analysis of the expressed MBP fusion protein library was performed using microtiter fluorometer Victor2 (Perkinelmer, USA), and the emission intensities of ECFP and EYFP were measured using a 450/8 nm excitation filter, a 480/10 nm emission filter and a 535/25 nm emission filter. An index of signal intensity was defined as the change of ratio ($\Delta$ratio) between the FRET efficiency ratio$_{10\ mM}$ in the presence of 10 mM maltose and the FRET efficiency (ratio$_{apo}$) in the absence of maltose.

Figure 5:
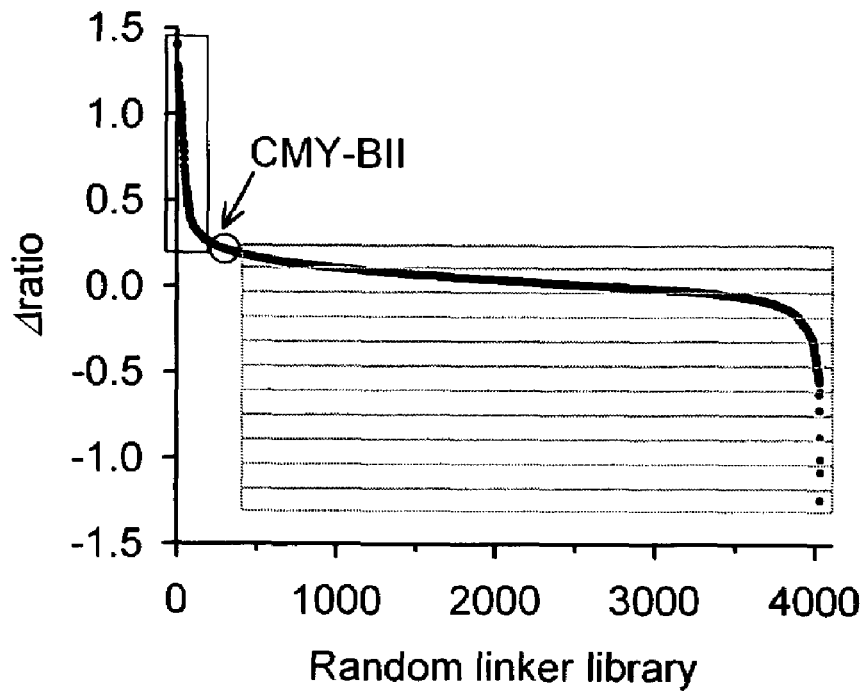
FIG. 5 is a graphic diagram showing ⊿ratio distributions screened from a fusion protein library constructed while randomly varying a linker peptide between ECFP and MBP (□: the distribution of fusion proteins having an increased sensitivity compared to that of CMY-BII; ▤: the distribution of fusion proteins having a decreased signal intensity compared to that of CMY-BII; and ○: the group of CMY-BII).
Figure 6:
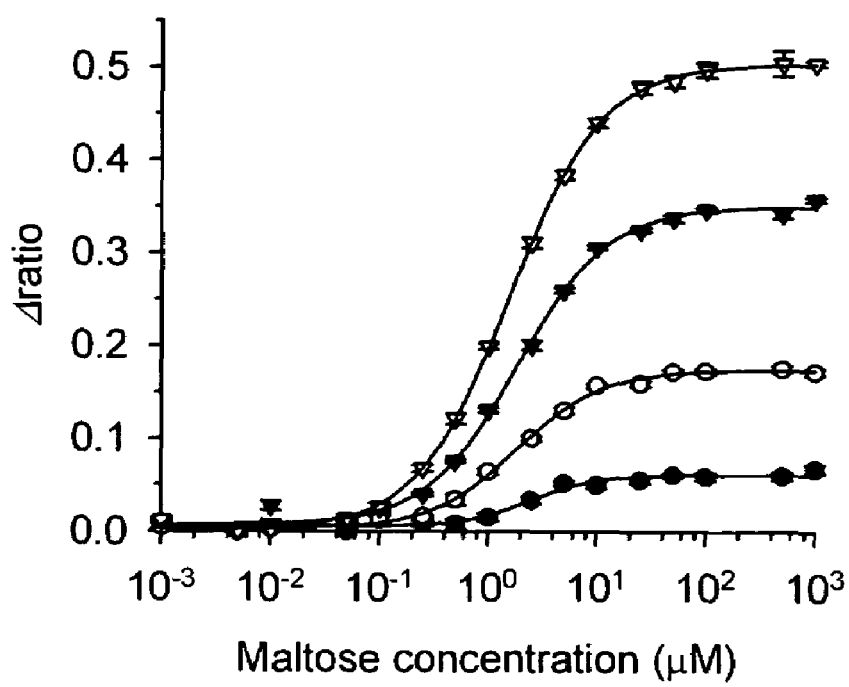
FIG. 6 is a diagram of Sigmoidal curves expressing a change in ⊿ratio of the inventive MBP fusion proteins according to a change in maltose concentration (●: CMY-0; ○: CMY-BII; ▼: CMY-QI; and ∇: CMY-LH).

The analysis results for the library of about 4000 MBP fusion proteins constructed while varying connecting peptides between ECFP and MBP are as follows. As shown in FIG. 5, the percentage of MBP fusion proteins having increased $\Delta$ratio compared to CMY-BII was about 5% or less, and as a result, fusion protein CMY-QI of SEQ ID NO: 31 and fusion protein CMY-LH of SEQ ID NO: 32, showing a great increase in $\Delta$ratio, could be selected. Accordingly, it was found that the ECFP and MBP of the CMY-QI were fused to each other by Gln-Ilu, and the ECFP and MBP of the CMY-LH were fused to each other by Leu-His. The ratio$_{apo}$ values of the CMY-QI and CMY-LH were found to be 1.96 and 3.02, respectively. Also, as can be seen in FIG. 6, the $\Delta$ratio values thereof were 0.34 and 0.5, respectively, which corresponded to about 7 and 10-fold increases in signal intensity, compared to CMY-0. This suggests that the MBP fusion proteins capable of quantitatively measuring the concentration of maltose in a more precise manner could be secured. As shown in Table 1, quantification range and $K_d$ which can be quantitatively measured using these MBP fusion proteins were similar to CMY-BII constructed in Example 3.

Example 5

Construction and Analysis of Fusion Proteins Having Mutations at Maltose Binding Site As disclosed in a previously published document, when the Trp62 of MBP is substituted with Ala, the $K_d$ of MBP and the quantification range for maltose can be changed (Martineau, P. et al., J. Mol. Biol. 214: 337, 1990). Thus, a MBP fusion protein expression vector library showing a change in the binding ability to maltose was constructed by performing genetic manipulation for substituting the Trp62 of MBP with a variety of amino acids.

To substitute the Trp62 of MBP playing an important role in binding to maltose with other kinds of amino acids, a mega-primer, in which the gene at the N-terminal end of MBP was amplified using a primer of SEQ ID NO: 13 having a substitution of NNN at a base sequence encoding the Trp62 of MBP and a primer of SEQ ID NO: 10, was amplified. Then, using the mega-primer and a primer of SEQ ID NO: 11, a full-length mutant MBP gene was amplified, and using a primer of SEQ ID NO: 5 and a primer of SEQ ID NO: 14 constructed such that Leu-His was produced between ECFP and MBP, the ECFP gene was amplified. The ECFP and mutant MBP genes were connected to each other by overlap-extension PCR and digested with NdeI and BamHI. The resulting genes were substituted and inserted into the pECMY-BII vector, thus constructing an expression vector library having a substitution of the mutant MBP gene.

The connection site between the ECFP and MBP genes of each of the MBP fusion proteins, and the gene mutation of the Trp62 position of the MBP, were analyzed for their base sequences using a primer of SEQ ID NO: 15.

The MBP fusion protein expression vector library constructed according to said method was transformed into E. coli JM109 (DE3) and then screened using microtiter fluorometer Victor2 (Perkin-elmer, USA). As a result, MBP fusion protein CMY-LH/W62A of SEQ ID NO: 33, MBP fusion protein CMY-LH/W62H of SEQ ID NO: 34 and MBP fusion protein CMY-LH/W62L of SEQ ID NO: 35 could be secured. The CMY-LH/W62A having a substitution of Trp62 with Ala in MBP was secured for use as a control group, the CMY-LH/W62H was found to have a substitution of Trp62 with His in MBP, and the CMY-LH/W62L was found to have a substitution of Trp62 with Leu in MBP.

Figure 7:
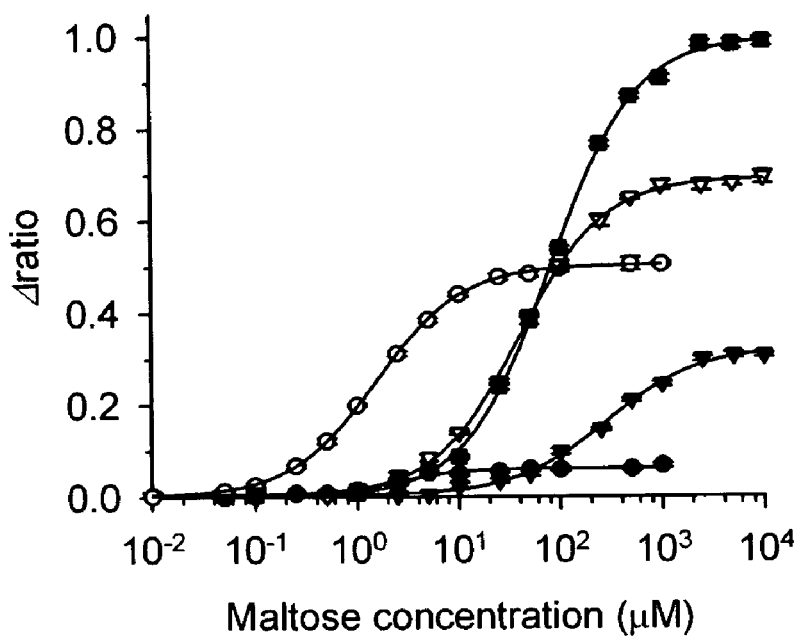
FIG. 7 is a diagram of Sigmoidal curves expressing a change in ⊿ratio of the inventive MBP proteins containing a mutation at Trp62 of MBP and having various quantification ranges for maltose (●: CMY-0; ○: CMY-LH; ▼: CMY-LH/W62A; ∇: CMY-LH/W62H; and ■: CMY-LH/W62L).

The ratio$_{apo}$ values of the CMY-LH/W62A, CMY-LH/W62H and CMY-LH/W62L were in the range of 2.66-2.81, which was slightly lower than that of CMY-LH. However, the $\Delta$ratio values showed great differences. Specifically, the CMY-LH/W62A, CMY-LH/W62H and CMY-LH/W62L showed the $\Delta$ratio values of 0.30, 0.69, and 1.00, respectively (Table 1, FIG. 7). These $\Delta$ratio values correspond to about 14-fold increase for CMY-LH/W62H and about 20-fold increase for CMY-LH/W62L, compared to that of CMY-0. The maltose concentration range and $K_d$, which can be quantitatively measured using these MBP fusion proteins, are summarized in Table 1 below. Thus, because the MBP fusion proteins were secured, the quantification of a wider range of maltose concentration became possible.

TABLE 1

Analysis results for characteristics of MBP fusion proteins

| Maltose sensors | $K_d^a$, µM | Quantification range[b], µM | ratio$_{apo}$[c] | Δratio[d] |
|---|---|---|---|---|
| CMY-0 | 2.4 ± 0.2 | 0.5-11.2 | 1.56 | 0.05 |
| CMY-B | — | — | 1.35 | — |
| CMY-BII | 1.8 ± 0.1 | 0.3-13.3 | 1.85 | 0.17 |
| CMY-QI | 1.8 ± 0.1 | 0.2-15.1 | 1.96 | 0.34 |
| CMY-LH | 1.6 ± 0.1 | 0.2-13.2 | 3.02 | 0.50 |
| CMY-LH/W62H | 40 ± 1 | 5-325 | 2.81 | 0.69 |
| CMY-LH/W62L | 80 ± 1 | 10-650 | 2.66 | 1.00 |
| CMY-LH/W62A | 255 ± 6 | 31-2,080 | 2.70 | 0.30 |

[a] $K_d$ of the fluorescent indicator proteins for detection of maltose was determined by fluorescence ratio. The points corresponding to 50% saturation were estimated as the dissociation constants for maltose.
[b] The range for quantification was defined as the range between 10 and 90% saturation of maltose.
[c] ratio$_{apo}$ was defined as the fluorescence ratio (530/480 nm) of fluorescent indicator proteins in the absence of maltose.
[d] Δratio was determined from the difference of ratio$_{10\ mM}$ and ratio$_{apo}$, where ratio$_{10\ mM}$ is the ratio at saturating maltose concentrations.

Figure 8A:
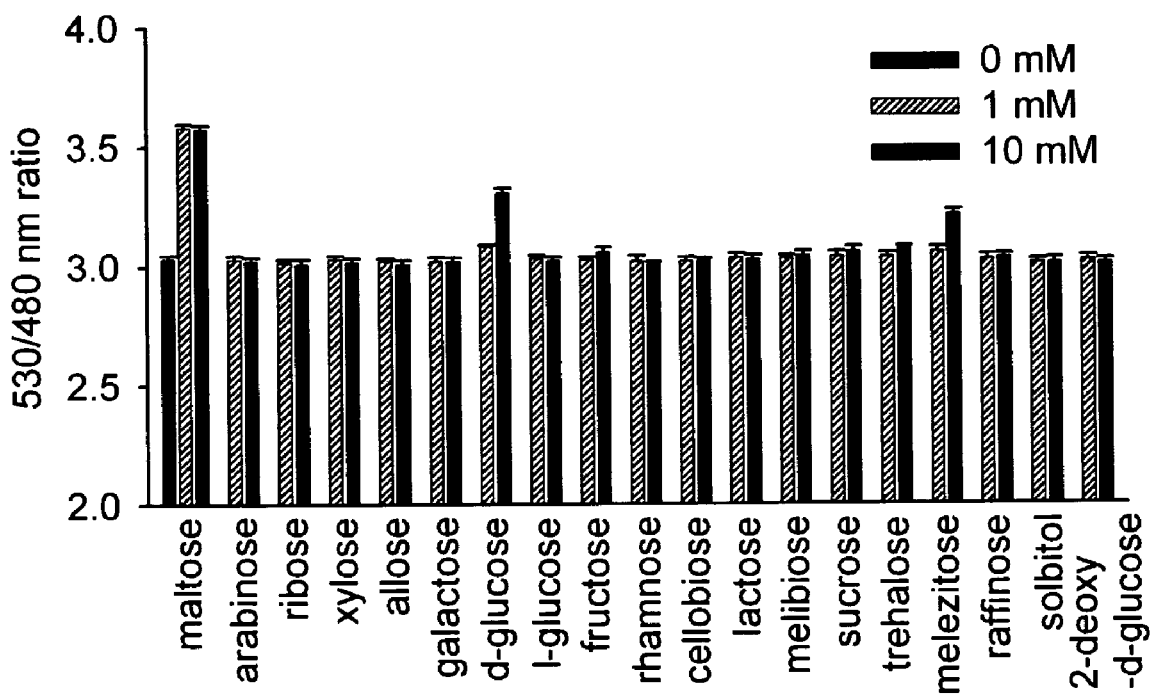
FIG. 8A: CYM-LH.
Figure 8B:
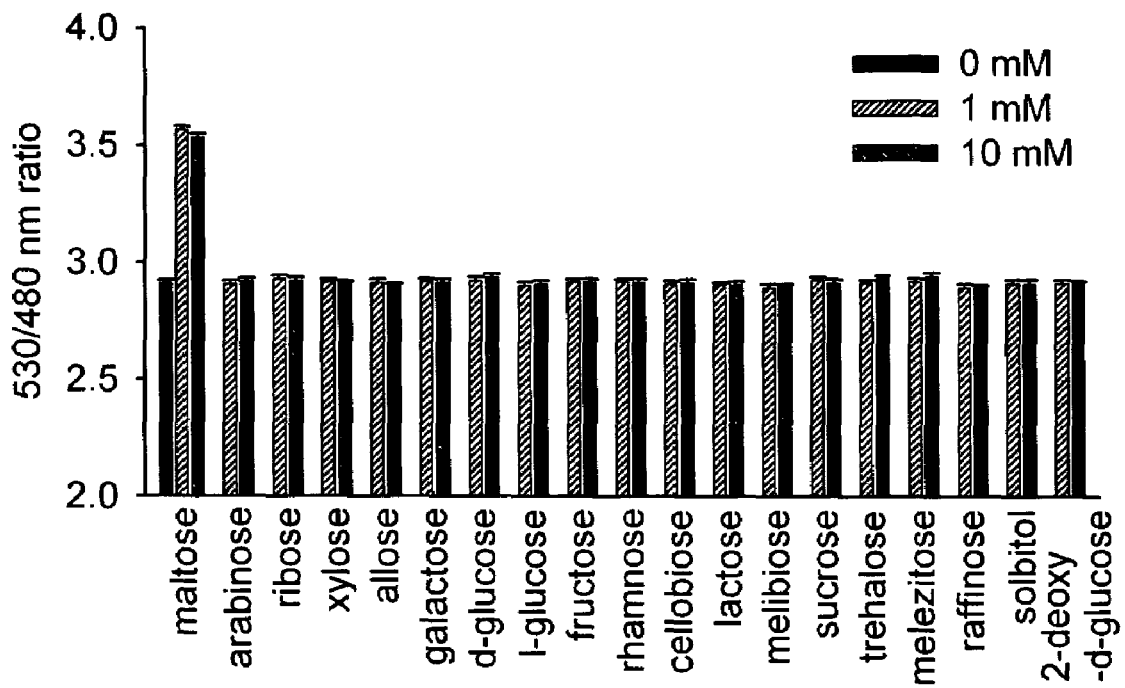
FIG. 8B: CMY-LH/W62H
Figure 8C:
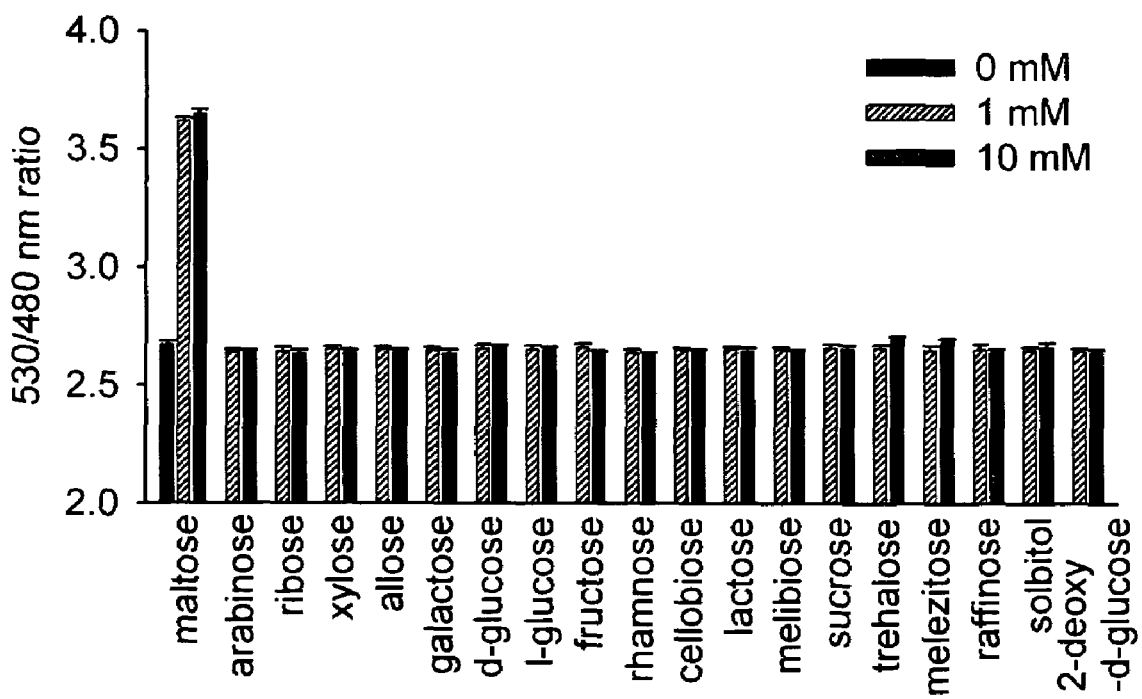
FIG. 8C: CMY-LH/W62L.

Meanwhile, in order to examine the substrate specificity of the three MBP fusion proteins (CMY-LH, CMY-LH/W62H and CMY-LH/W62L) having a difference in the binding ability to maltose, among the MBP fusion proteins, whether a variety of mono-, di-, trisaccharides and sugar alcohols were bound to the three fusion proteins was analyzed using the method of Example 3. FIG. 8A-C shows the comparison of the affinities of MBP fusion proteins for substrates. As shown in FIG. 8A, most sugars except for maltose did not show the binding to the MBP fusion protein, but d-glucose and melezitose showed a low level of affinity at an increased concentration of 10 mM. This change of ratio (Δratio) is attributable to contamination of trace maltose, because d-glucose is produced by hydrolysis of carbohydrates bound in maltose unites (Guntas, G. et al., *J. Mol. Biol.*, 336:263-273, 2004). FIGS. 8B and 8C show the comparison of the affinities of CMY-LH/W62H and CMY-LH/W62L for substrates. As shown in the drawings, the fusion proteins did not show an affinity for all sugars except for maltose, regardless of concentration.

The above results demonstrated that the MBP fusion proteins show the ability to specifically bind only to maltose, and can be effectively used to quantitatively measure intracellular maltose concentration through the microscopic analysis of living cells without interference from other sugars.

Example 6

Imaging Analysis Using MBP Fusion Proteins in Yeasts

To analysis of maltose uptake in living yeast and the change in intracellular maltose concentration using MBP fusion proteins, an expression vector was constructed in the following manner. As an expression vector, YEGα-HIR525 (Sohn et al., *Process Biochemistry*, 30:653, 1995) was used, and to construct a yeast expression vector, a GAL promoter gene was amplified from YEGα-HIR525 using primers of SEQ ID NO: 16 and SEQ ID NO: 17 constructed such that SacI and NdeI restriction enzyme sites were inserted into the 5'- and 3'-terminal ends of the GAL promoter.

Figure 9:
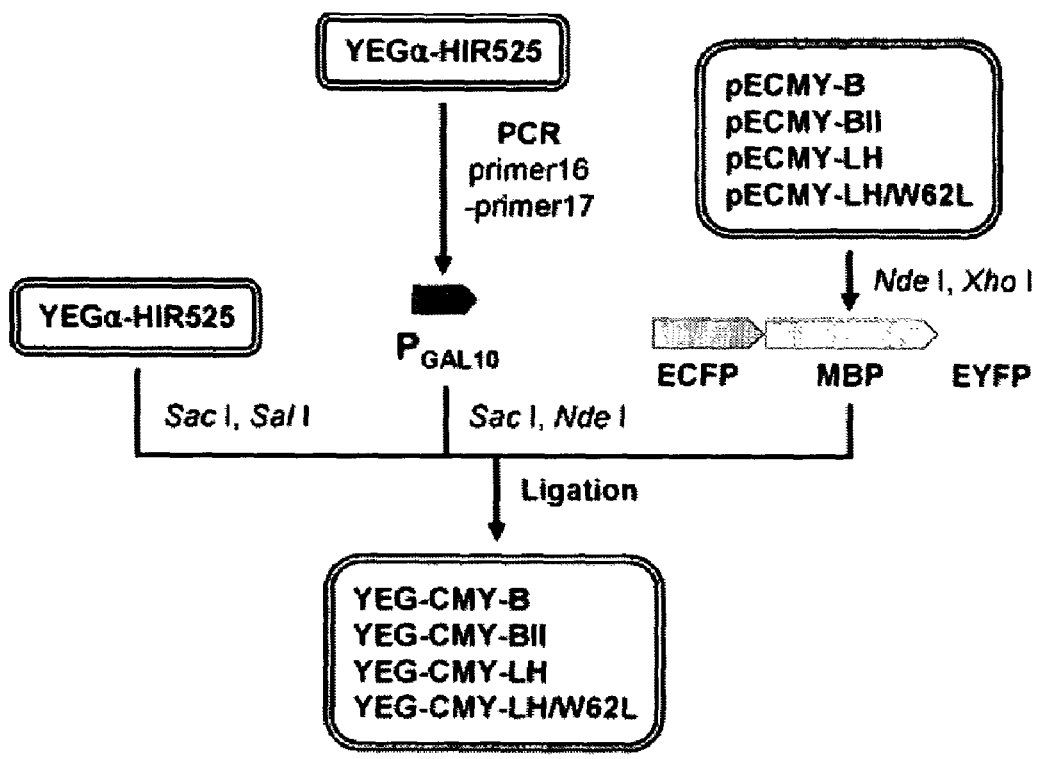
FIG. 9 is a flow diagram showing a process of constructing yeast expression vectors, which are used to observe a change in the concentration of maltose absorbed or metabolized in living yeast cells.

The GAL promoter gene was digested with SacI and NdeI restriction enzymes, and genes encoding MBP fusion proteins of pECMY-B, pECMY-BII, pECMY-LH and pECMY-LH/W62L were cut with NdeI and SalI restriction enzymes and then inserted into YEGα-HIR525 digested with SacI and SalI restriction enzymes, thus constructing yeast expression vectors, termed "YEG-CMY series" (FIG. 9).

To quantitatively measure the concentration of maltose absorbed into yeasts by imaging analysis, each of the MBP fusion protein vectors was transformed into host Haploid *Saccharomyces cerevisiae* 2805 (Mat a prep4::HIS3 prb1 can1 his3 ura3) (Sohn et al., *Process Biochemistry*, 30:653, 1995). The *S. cerevisiae* 2805 cells transformed with each of the above-constructed YEG-CMY series vectors were cultured using 1% glucose as a carbon source and 1% galactose as an inducer in SD medium consisting of 0.67% yeast nitrogen base (BD Bioscience, USA) without containing amino acid and 0.077% -Ura DO supplement (BD Bioscience, USA) for 30-40 hours.

To deplete the remaining carbon source before imaging, the harvested yeasts were dispersed in a sugar-free SD medium (pH 7.4) and cultured for about 2 hours. Then, 25 µl of culture broth were transferred into 5 ml of sugar-free SD media in a glass-bottomed dish (35×10 mm, SPL, Korea) and left to stand for about 1 hour. Dishes containing the cells were fixed on the microscope stage with both-sided tapes, to avoid disturbing the cell sediments during the microscopic observations.

The imaging was carried out using an FRET split imaging system consisting of a DP30BW high-sensitivity CCD (Charge Coupled Device) camera (Olympus, Japan) connected to a split primary image camera port (U-SIP), and an IX71 inverted microscope (Olympus, Japan), and the observation of the yeasts was performed using PlanApo N 60x, 1.42 na, oil-immersion objective lens (Olympus, Japan). The storage and analysis of images observed with the microscope were performed using Cell$^P$ software (Olympus, Japan), and as a FRET filter set for observing ratio imaging resulting from the FRET of living yeasts, XF88-2 (Omega Optical, USA) consisting of 440AF21 excitation, 455DRLP dichroic mirror, and 480AF30 and 535AF26 emission filters was used.

The quantitative measurement of the concentration of maltose absorbed into yeasts was carried out by observing fluorescent images through the CCD camera placed on the fluorescent microscope, taking the fluorescent images at 30-second intervals for 10 minutes and storing and quantitatively analyzing the taken images with the Cell$^P$ software (Olympus). The supply of maltose was conducted such that it reached an overall concentration of 10 mM after 2 minutes from the start of observation, and the change in intracellular maltose concentration with the passage of time was analyzed by comparing emission intensities of EYFP and ECFP.

Figure 10A:
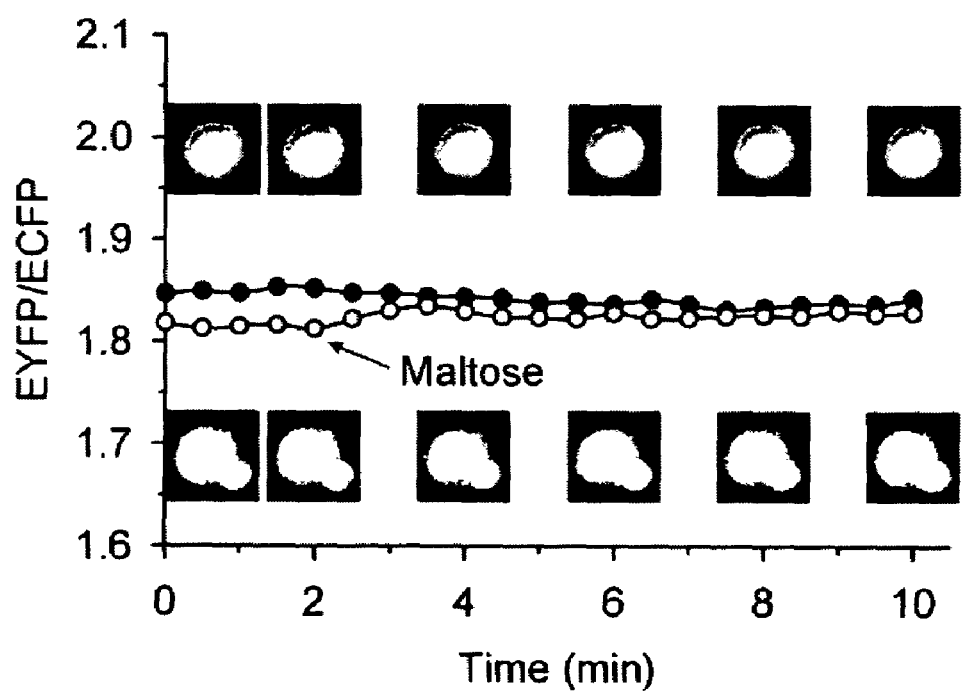
FIG. 10A shows results for yeast having CMY-B expressed therein.

FIG. 10A shows imaging analysis results for yeasts expressing CMY-B having no sensitivity to maltose. As shown in FIG. 10A, there was no difference between the ratio$_{apo}$ of yeast to which maltose was not added, and the ratio$_{10\ mM}$ of yeast to which maltose was added to a saturation concentration of 10 mM after 2 minutes. Thus, using the analysis result shown in FIG. 10A as a control group, a change in FRET according to the concentration of maltose in yeast, in which other kinds of MBP fusion proteins were expressed, was analyzed.

Figure 10B:
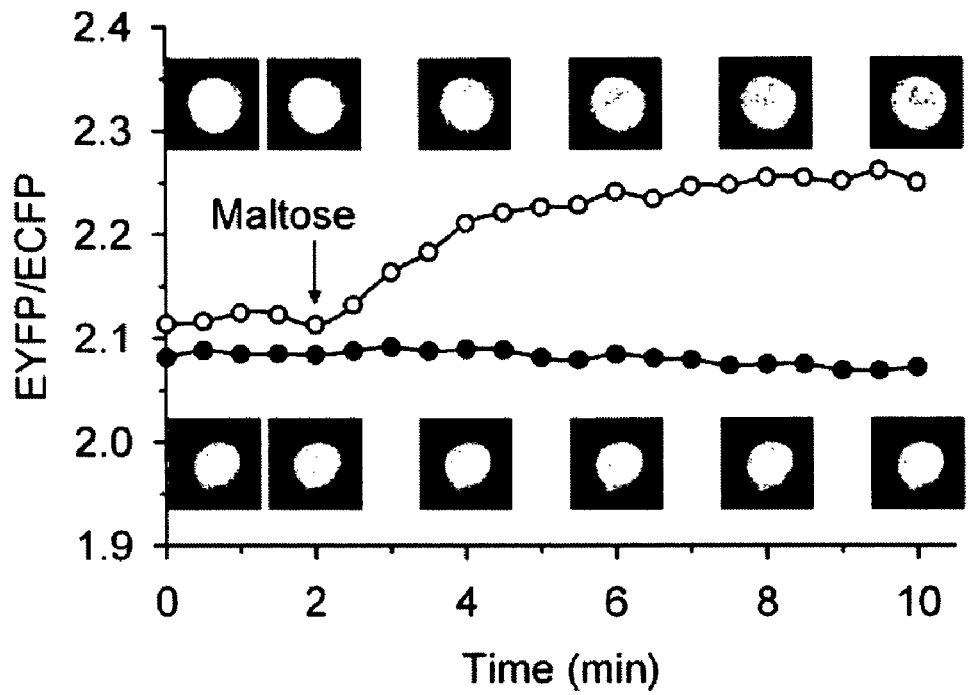
FIG. 10B shows results for yeast having CMY-BII expressed therein.

FIG. 10B shows imaging results for yeast having CMY-BII expressed therein. As shown in FIG. 10B, there was a difference in ratio between a condition where maltose was not added, and a condition where 10 mM of maltose was added after 2 minutes. About 2 minutes after the addition of maltose, intracellular maltose concentration reached a saturation state.

Figure 10C:
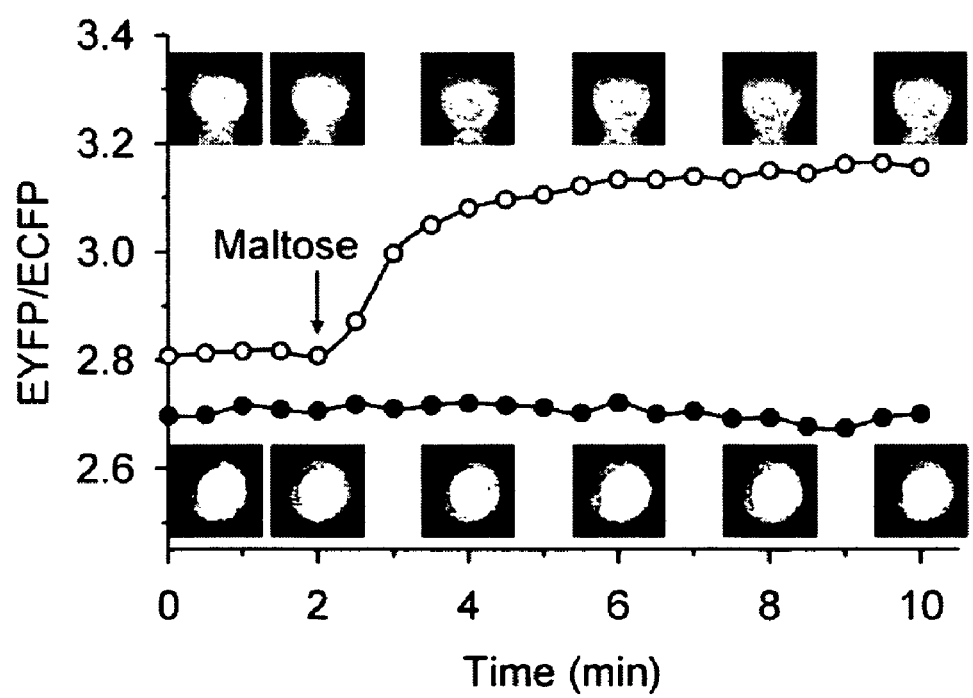
FIG. 10C shows results for yeast having CMY-LH expressed therein.

FIG. 10C shows analysis results for the expression of CMY-LH. As shown in FIG. 10C, a change in ratio obtained by adding 10 mM of maltose after 2 minutes was at least 2 times higher than that of the yeast having CMY-BII expressed therein. This demonstrates that the MBP fusion protein having an increased signal intensity resulting from the optimization of the connecting peptide between ECFP and MBP is applied to not only in vitro, but also in vivo.

Figure 10D:
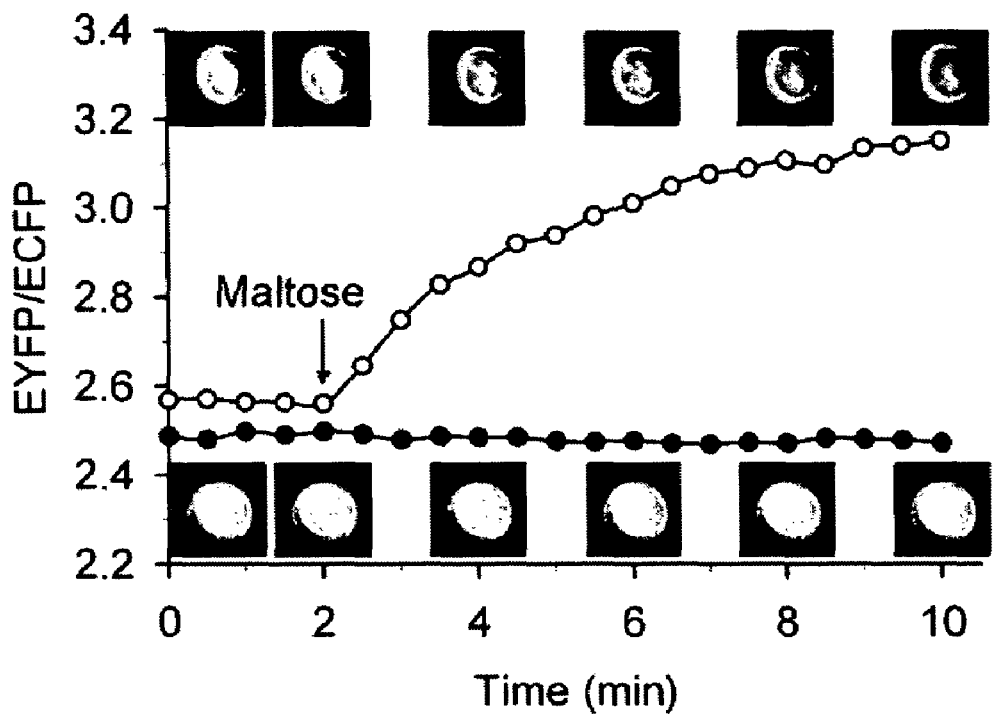
FIG. 10D shows CMY-LH/W62L expressed therein (●: the emission intensity ratio of yeast in the absence of maltose; and ○: the emission intensity ratio of yeast to which 10 mM of maltose was added 2 minutes after the first observation time point).

FIG. 10D shows imaging results for yeast having CMY-LH/W62L expressed therein. As shown in FIG. 10D, a change in ratio was higher than that of CMY-LH, similarly to the in vitro measurement results. However, unlike the results shown in FIG. 10B or 10C, the intracellular maltose concentration did not reach a saturation state even after 10 minutes, because the $K_d$ of CMY-LH/W62L was increased to 80 µM. Thus, the range of quantitative measurement of maltose absorbed or metabolized into in vivo was greatly enlarged, and thus a change in ligand concentration at a physiological level can be measured without a limitation on an upper limit.

Example 7

Construction of Fluorescent Indicator Proteins Using Various PBPs

To develop fluorescent indicator proteins for detecting various substances, genetic manipulation was carried out by introducing E. coli-derived PBPs which are similar to each other conformationally and functionally into the MBP position of the fluorescent indicator protein for detection of maltose.

The selection of PBPs to be introduced into the MBP position was performed by collecting data from SCOP (Structural Classification of Proteins; http://scop.mrc-lmb.cam.ac.uk/scop/), and then investigating the kinetic change of three-dimensional structures which is accompanied by substrate binding in PDB (Protein Data Bank, http://www.rcsb.org/pdb/). For example, three kinds of E. coli-derived PBPs such as ALBP, RBP, and ARBP were introduced into the MBP site of the MBP fusion proteins according to the present invention. For this purpose, the genetic sequence information of said PBPs was secured from Swiss-Prot (http://kr.expasy.org/), and on the basis of the information, primers capable of amplifying genes encoding the PBPs were constructed. The genes were amplified by performing PCR from the chromosome of E. coli MG1655 using the constructed primers.

In amplification for constructing ALBP fusion protein expression vectors, the ECFP gene was amplified using primers of SEQ ID NO: 5 and SEQ ID NO: 18, and the ALBP gene was amplified using primers of SEQ ID NO: 19 and SEQ ID NO: 20. The amplified ECFP and ALBP genes were amplified into ECFP-ALBP genes by overlap-extension PCR using primers of SEQ ID NO: 5 and SEQ ID NO: 20. Thus, like the MBP fusion proteins, due to six N bases between ECFP and ALBP, various peptides having various combinations of two amino acids between ECFP and ALBP could be produced. Using the ECFP-ALBP genes, a library was constructed by inserting the ECFP-ALBP genes into a pECMY-BII expression vector from which the ECFP-MBP gene has been removed using NdeI and BamHII restriction enzyme recognition sites. Likewise, in amplification for constructing ARBP fusion protein expression vectors, the ECFP gene was amplified using primers of SEQ ID NOs: 5 and 21, and the ARBP gene was amplified using primers of SEQ ID NOs: 22 and 23. The amplified ECFP and ARBP genes were connected with each other by overlap-extension PCR using primers of SEQ ID NOs: 5 and 23 so as to prepare an ECFP-ARBP gene. The gene was inserted into the ECFP-MBP gene position of a pECMY-BII expression vector, thus constructing a library. Also, in amplification for constructing RBP fusion protein expression vectors, the ECFP gene was amplified using primers of SEQ ID NOs: 5 and 24, and the RBP gene was amplified using primers of SEQ ID NOs: 25 and 26. The amplified ECFP and RBP genes were connected with each other by overlap-extension PCR using primers of SEQ ID NOs: 5 and 26 so as to prepare an ECFP-RBP gene. The prepared gene was inserted into the ECFP-MBP gene position of a pECMY-BII vector, thus constructing a library.

Figure 11A:
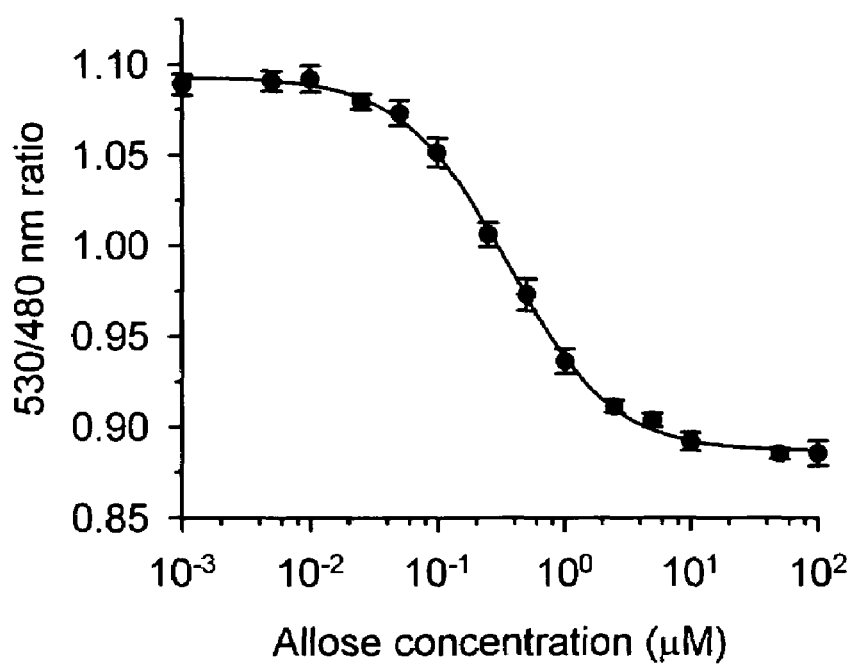
FIG. 11A: CalsBY-QV.
Figure 11B:
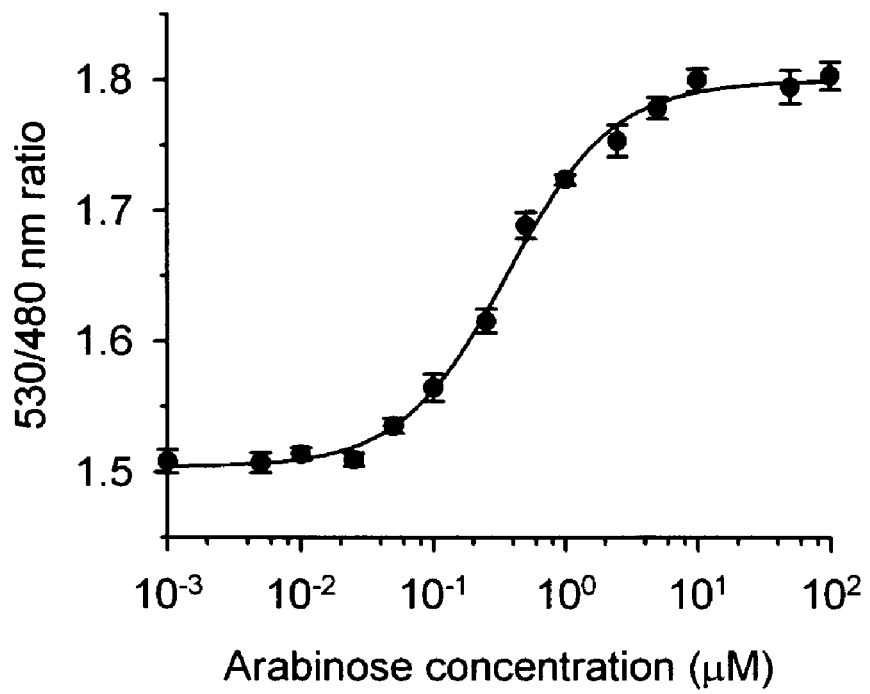
FIG. 11B: CaraFY-PR.
Figure 11C:
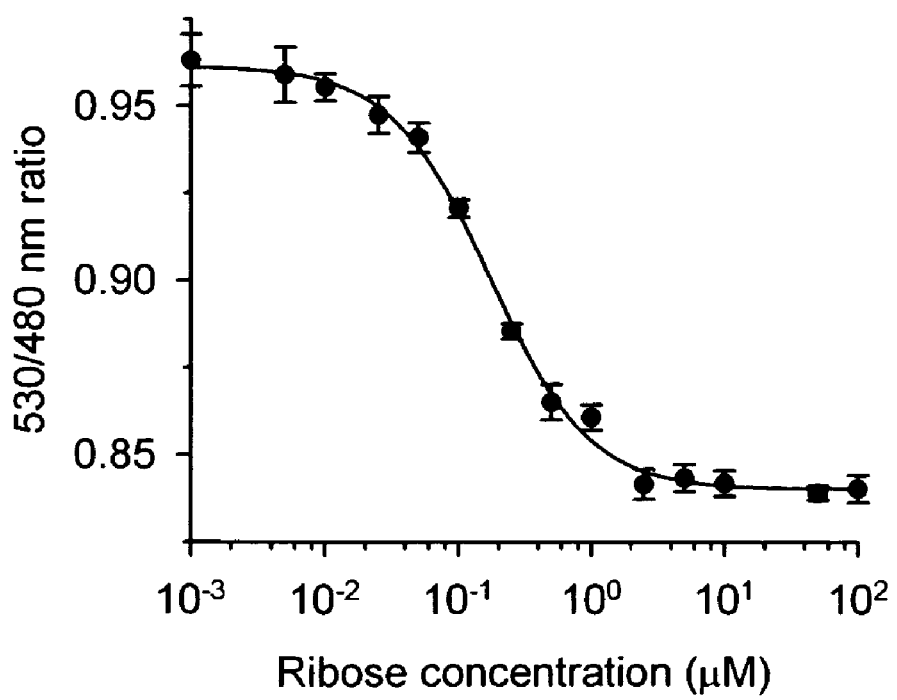
FIG. 11C: CrbsBY-ND.

The fusion protein expression vectors constructed in the form of libraries as described above were transformed into E. coli JM109 (DE3), and 3-5 bacterial strains transformed with vectors were randomly selected from each of the libraries without carrying out the screening process described in Example 4, and were expressed and purified according to the method of Example 2. Then, the various PBP fusion proteins were subjected to analyze the fluorescence characteristics to each of substances, and sugar sensors (the fluorescent indicator proteins for detection of sugar) having the highest signal intensity were selected. As a result, as shown on FIGS. 11A, 11B and 11C, and Table 2 below, CalsBY-QV of SEQ ID NO: 36, CaraFY-PR of SEQ ID NO: 37 and CrbsBY-ND of SEQ ID NO: 38 could be secured.

TABLE 2

Analysis results for characteristics of PBP fusion proteins

| Sugar sensors | $K_d^a$, µM | Quantification range[b], µM | ratio$_{apo}$[c] | $\Delta$ratio[d] |
|---|---|---|---|---|
| CalsBY-QV | 0.35 ± 0.02 | 0.04-2.81 | 1.09 | −0.21 |
| CaraFY-PR | 0.36 ± 0.01 | 0.05-2.74 | 1.50 | 0.29 |
| CrbsBY-ND | 0.17 ± 0.01 | 0.03-1.15 | 0.96 | −0.12 |

[a]$K_d$ of the fluorescent indicator proteins for detection of sugar were determined by fluorescence ratio. The points corresponding to 50% saturation were estimated as the dissociation constants for sugar.
[b]The range for quantification was defined as the range between 10 and 90% saturation of sugar.
[c]ratio$_{apo}$ was defined as the fluorescence ratio (530/480 nm) of fluorescent indicator proteins in the absence of sugars.
[d]$\Delta$ratio was determined from the difference of ratio$_{10\,mM}$ and ratio$_{apo}$, where ratio$_{10\,mM}$ is the ratio at saturating sugar concentrations.

The DNA sequences of said fusion proteins were analyzed and, as a result, it was observed that the ECFP and ALBP of CalsBY-QV were fused to each other by Gln-Val, the ECFP and ARBP of CaraFY-PR were fused to each other by Pro-Arg, and the ECFP and RBP of CrbsBY-ND were fused to each other by Asn-Asp. The CalsBY-QV or CrbsBY-ND fusion protein showed a reduction in $\Delta$ratio due to binding of allose or ribose, because both ends of the binding protein were far away from each other due to binding of the substance, unlike MBP or ARBP (Chaudhuri, B. N. et al., J. Mol. Biol., 286:1519, 1999; Magnusson, U. et al., J. Bio. Chem., 277:14077, 2002).

Figure 12A:
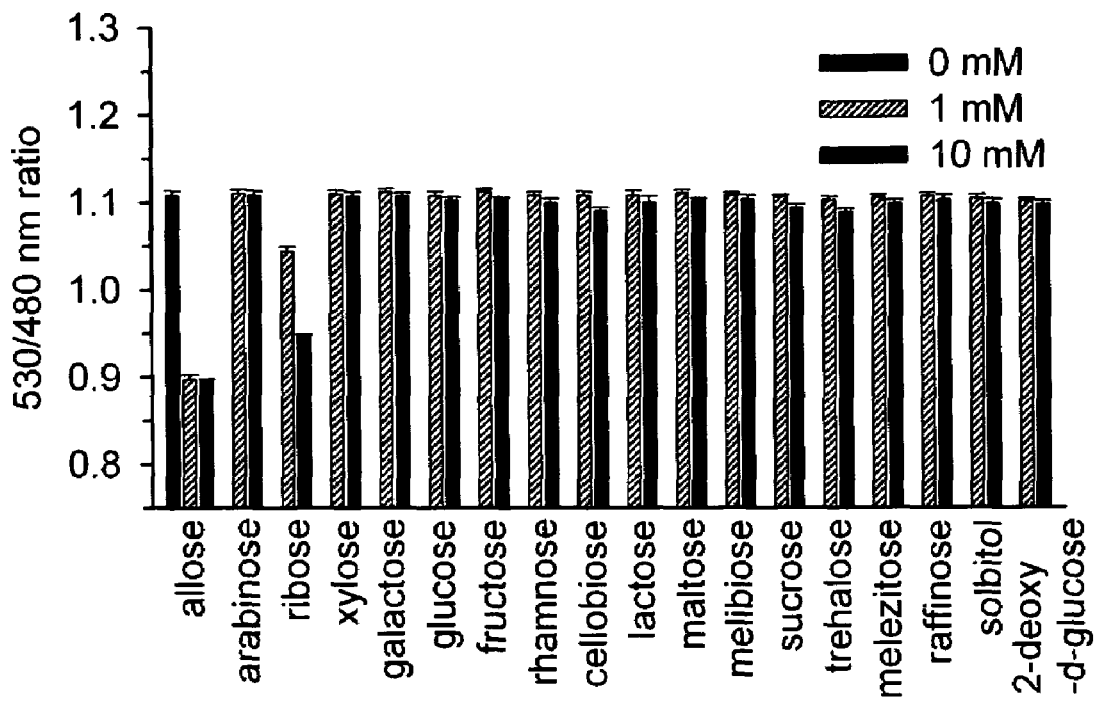
FIG. 12A: for CalsBY-QV.
Figure 12B:
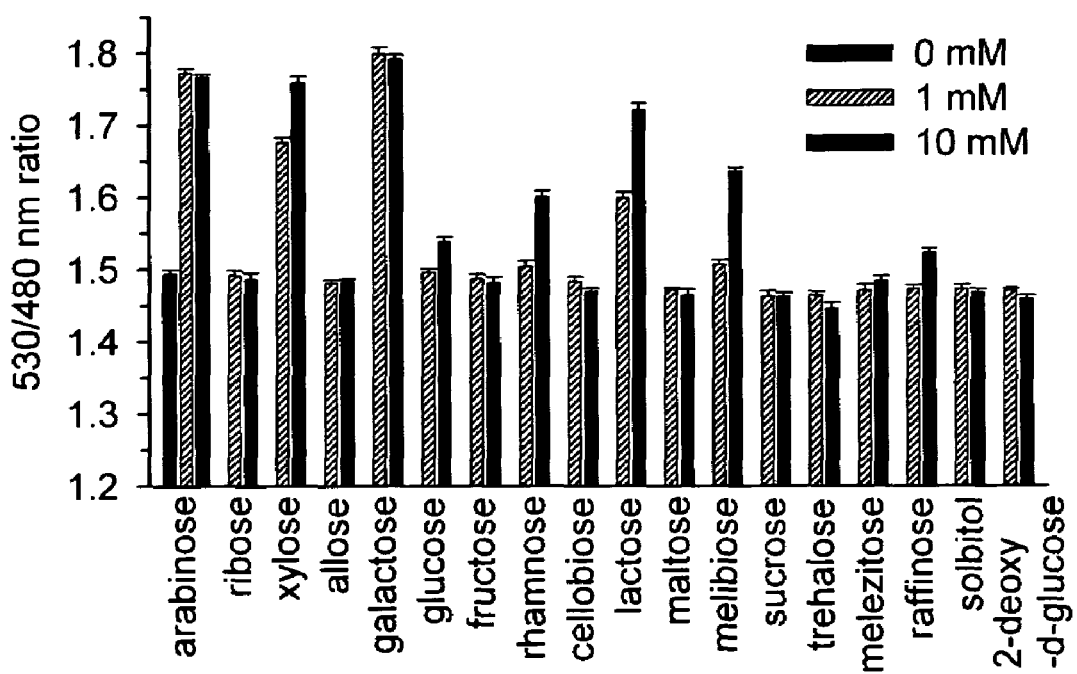
FIG. 12B: for CaraFY-PR
Figure 12C:
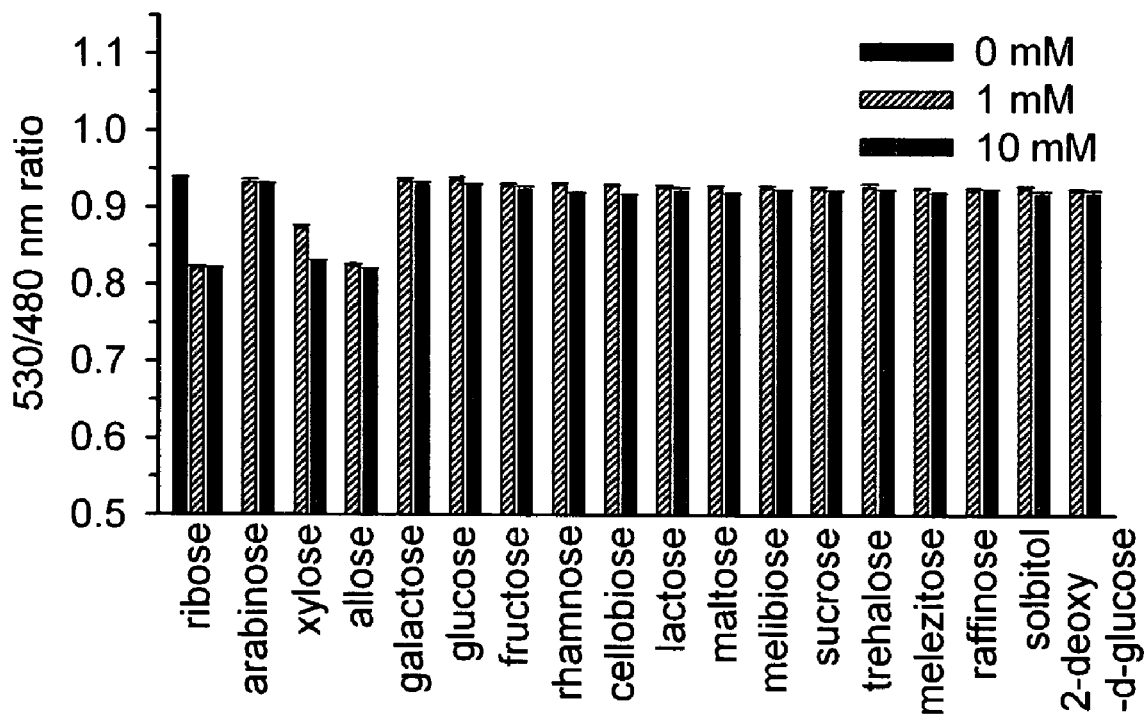
FIG. 12C: for CrbsBY-ND.

To examine the substrate affinity of said three kinds of fusion proteins, the substrate specificity thereof for a variety of sugars was analyzed. FIG. 12A shows the comparison of the affinities of CalsBY-QV for substrates. As shown in FIG. 12A, although the binding to ALBP fusion protein was not shown in most sugars except for allose, ribose showed a low affinity for ALBP fusion protein at an increased concentration of mM levels (Chaudhuri, B. N. et al., J. Mol. Biol., 286:1519, 1999). On the other hand, FIG. 12C shows the comparison of the affinities of CrbsBY-ND for substrates. As shown in FIG. 12C, most of the sugars had no affinity for RBP fusion protein, but they showed a very high affinity for allose, and xylose also had a significant affinity, although it showed lower affinity than that of allose (Kim, C. H. et al., *J. Bacteriol.*, 179:7631, 1997). FIG. 12B shows the comparison of the affinities of CaraFY-PR for substrates. As shown in FIG. 12B, the ARBP fusion protein showed a relatively low substrate specificity compared to those of other kinds of fusion proteins. Particularly, it showed a very high affinity for galactose (Fukada, H. et al., *J. Biol. Chem.*, 258:13193, 1983), and also had a low affinity for xylose, rhamnose, lactose and melibiose.

Example 8

Construction of Fluorescent Indicator Proteins Using SBP

The SBP gene made by partially mutating the previously reported MBP gene (Guntas, G. et al., *PNAS*, 102:11224, 2005) was substituted into the MBP gene position of the MBP fusion protein expression vector.

The MBP-encoding gene to be used as a template was a pMALc2x vector (NEB, USA), and to make the SBP gene, PCR was performed using primers of SEQ ID NOs: 27, 28, 29 and 11. Because the above-amplified gene contains partial mutations in MBP, including a substitution of Asp14 with Leu, a substitution of Lys15 with Phe, a substitution of Trp62 with Tyr, and a substitution of Glu111 with Tyr, it encodes the SBP gene capable of binding to sucrose, as reported in the prior art (Guntas, G. et al., *PNAS*, 102:11224, 2005).

To construct a CSY-B expression vector, the ECFP gene amplified using primers of SEQ ID NOs: 5 and 6 and the SBP gene were connected with each other by overlap-extension PCR using primers of SEQ ID NOs: 5 and 11 so as to make an ECFP-SBP gene. The gene was inserted into the ECFP-MBP gene position of the pECMY-BII expression vector, thus constructing a pECSY-B. Likewise, to construct a CSY-BII expression vector, the ECFP gene amplified using primers of SEQ ID NOs: 5 and 8 and the SBP gene were connected with each other by overlap-extension PCR using primers of SEQ ID NOs: 5 and 11 to make an ECFP-SBP gene. The ECFP-SBP gene was inserted into the ECFP-MBP gene position of the pECMY-BII expression vector, thus constructing a pECSY-BII vector. Also, to construct a CSY-LH expression vector, the ECFP gene amplified using primers of SEQ ID NOs: 5 and 14 and the SBP gene were connected with each other by overlap-extension PCR using primers of SEQ ID NOs: 5 and 11 so as to make an ECFP-SBP gene. The ECFP-SBP gene was inserted into the ECFP-MBP gene position of the pECMY-BII expression vector, thus constructing a pECSY-LH vector.

Figure 13A:
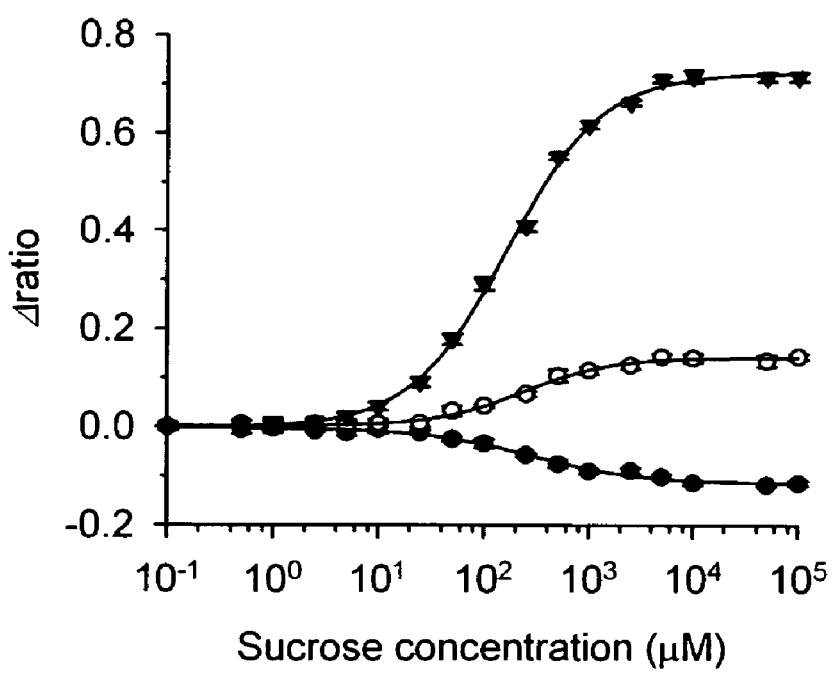
FIG. 13A is a graphic diagram for sucrose.
Figure 13B:
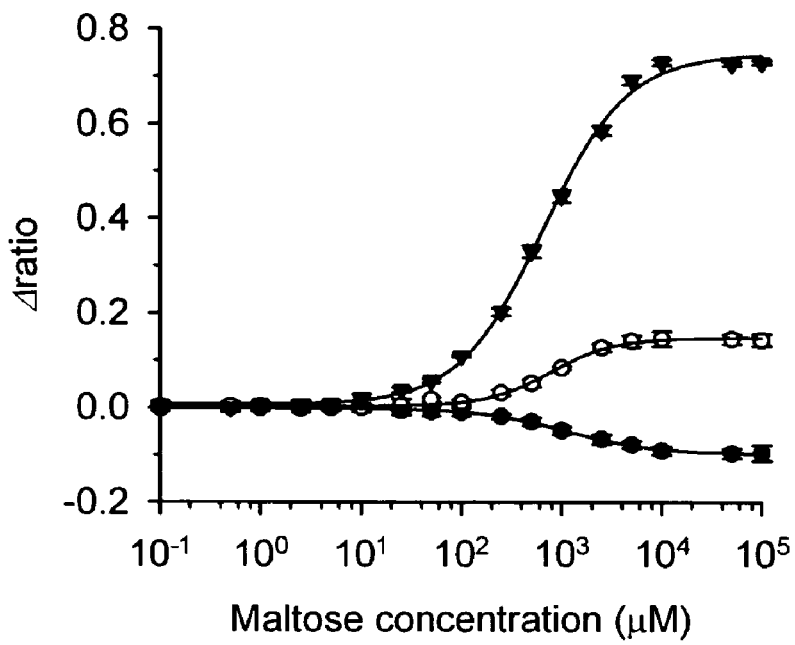
FIG. 13B is a graphic diagram for maltose (●: CSY-B; ○: CSY-BII; and ▼: CSY-LH).

The above SBP fusion protein expression vectors were transformed into *E. Coli* JM109 (DE3), expressed and purified according to the method of Example 3. Then the various SBP fusion proteins subjected to fluorescence analysis in order to analyze the signal intensity thereof to sucrose and maltose, and the characteristics of each of the SBP fusion proteins were analyzed. As a result, as shown in FIGS. 13A and 13B, and Table 3 below, among various SBP fusion proteins, CSY-LH of SEQ ID NO: 39 having the highest signal intensity to sucrose, was secured.

TABLE 3

Analysis results for characteristics of SBPP fusion proteins

| Sucrose sensors | | $K_d{}^a$, µM | Quantification range$^b$, µM | ratio$_{apo}{}^c$ | Δratio$^d$ |
|---|---|---|---|---|---|
| CSY-B | sucrose | 286 ± 16 | 20-3,700 | 1.56 | −0.11 |
| | maltose | 1,132 ± 183 | 120-9,500 | 1.55 | −0.10 |
| CSY-BII | sucrose | 234 ± 18 | 30-1,880 | 1.64 | 0.14 |
| | maltose | 773 ± 69 | 155-3,800 | 1.65 | 0.14 |
| CSY-LH | sucrose | 163 ± 3 | 17-1,560 | 1.83 | 0.72 |
| | maltose | 640 ± 21 | 80-5,080 | 1.83 | 0.74 |

$^a$$K_d$ of the fluorescent indicator proteins for detection of sugar was determined by fluorescence ratio. The points corresponding to 50% saturation were estimated as the dissociation constants for sugar.
$^b$The range for quantification was defined as the range between 10 and 90% saturation of sugar.
$^c$ratio$_{apo}$ was defined as the fluorescence ratio (530/480 nm) of fluorescent indicator proteins in the absence of sugar.
$^d$Δratio was determined from the difference of ratio$_{10\ mM}$ and ratio$_{apo}$, where ratio$_{10\ mM}$ is the ratio at saturating sugar concentrations.

As can be seen in Table 3 above, the SBP fusion protein CSY-LH, to which the same connecting peptide between both ends of MBP of the CMY-LH having the highest signal intensity was applied intact, showed the highest Δratio. Thus, it was found that, when the optimized connecting peptide of CMY-LH is used intact in constructing a fluorescent indicator protein having new binding ability using MBP as a template, it is possible to construct a fusion protein having new function of excellent signal intensity. However, the $K_d$ values for sucrose and maltose, measured on the basis of CSY-LH, were about 25-fold higher compared to the previously reported results (Guntas, G. et al., *PNAS*, 102:11224, 2005).

Figure 14:
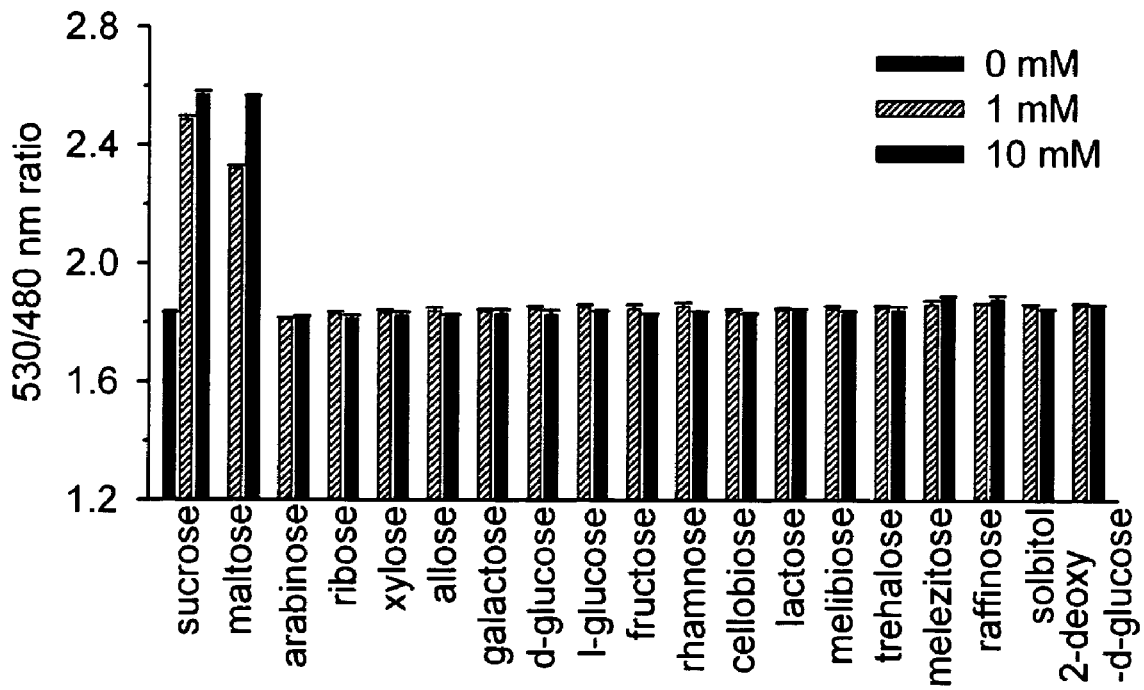
FIG. 14 is a graphic diagram showing analysis results for binding affinity to various sugars, conducted for CSY-LH having the most excellent signal intensity among SBP fusion proteins.

The CSY-LH was analyzed for binding affinity for a variety of sugars. As shown in FIG. 14, the CSY-LH did not bind to most of the sugars except for sucrose and maltose, like the previously reported results (Guntas, G. et al., *PNAS*, 102: 11224, 2005).

As described and proven above in detail, the present invention provides the fluorescent indicator proteins having an increased signal intensity to sugar concentration, based on the principle of FRET, which have excellent signal intensity compared to the prior fluorescent indicator proteins, and thus can more precisely measure the intracellular concentration of various sugars, including maltose. Also, according to the present invention, the preparation of fluorescent indicator proteins for detecting other sugars in addition to maltose became possible. In addition, the present invention can be effectively used to prepare fluorescent indicator proteins having an increased signal intensity from proteins used as biosensors in the prior art, and thus can be more generally applied.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A fluorescent indicator protein having an increased sensitivity to the concentration of sugars, which is represented by Formula I:

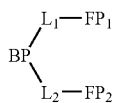

[Formula I]

wherein: BP (binding protein) is MBP (maltose binding protein) consisting of SEQ ID NO: 30; $L_1$ and $L_2$ consist of two amino acids, wherein $L_1$ is Leu-His and $L_2$ is Gly-Ser and wherein $L_1$ is attached to the N-terminal end of BP and $L_2$ is attached to the C-terminal end of BP; $FP_1$ is selected from the group consisting of ECFP (enhanced cyan fluorescent protein), EBFP (enhanced blue fluorescent protein) and EGFP (enhanced green fluorescent protein), and $FP_2$ is selected from the group consisting of EYFP (enhanced yellow fluorescent protein), EGFP (enhanced green fluorescent protein) and RFP (red fluorescent protein).

2. A fluorescent indicator protein, having an increased sensitivity to the concentration of sugars, which is represented by Formula I:

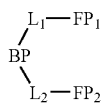

[Formula I]

wherein: said BP (binding protein) is MBP (maltose binding protein) consisting of SEQ ID NO: 30; $L_1$ and $L_2$ consist of two amino acids; $L_1$ is Gln-Ile or Leu-His and $L_2$ is Gly-Ser; said $L_1$ is attached to the N-terminal end of BP and $L_2$ is attached to the C-terminal end of BP; $FP_1$ is ECFP (enhanced cyan fluorescent protein), and $FP_2$ EYFP (enhanced yellow fluorescent protein); and wherein said fluorescent indicator protein consisting of an amino acid sequence set forth in SEQ ID NO: 31 or SEQ ID NO: 32.

3. A fluorescent indicator protein having an increased sensitivity to the concentration of sugars, which is represented by Formula I:

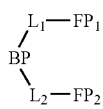

[Formula I]

wherein BP is a MBP mutant which has a mutation at position 62 in the amino acid sequence of SEQ ID NO: 30; $L_1$ and $L_2$ consist of two amino acids, wherein $L_1$ is Leu-His and $L_2$ is Gly-Ser and wherein $L_1$ is attached to the N-terminal end of BP and $L_2$, is attached to the C-terminal end of BP; $FP_1$ is selected from the group consisting of ECFP (enhanced cyan fluorescent protein), EBFP (enhanced blue fluorescent protein) and EGFP (enhanced green fluorescent protein), and $FP_2$ is selected from the group consisting of EYFP (enhanced yellow fluorescent protein), EGFP (enhanced green fluorescent protein) and RFP (red fluorescent protein).

4. A fluorescent indicator protein having an increased sensitivity to the concentration of sugars, which is represented by Formula I:

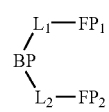

[Formula I]

wherein the BP is a MBP mutant which is selected from a group consisting of Trp62Ala, Trp62His and Trp62Leu in the amino acid sequence set forth in SEQ ID NO: 30; $L_1$ and $L_2$ consist of two amino acids, wherein $L_1$ is Leu-His and $L_2$ is Gly-Ser and wherein $L_1$ is attached to the N-terminal end of BP and $L_2$ is attached to the C-terminal end of BP: $FP_1$ is selected from the group consisting of ECFP (enhanced cyan fluorescent protein), EBFP (enhanced blue fluorescent protein) and EGFP (enhanced green fluorescent protein), and $FP_2$ is selected from the group consisting of EYFP (enhanced yellow fluorescent protein), EGFP (enhanced green fluorescent protein) and RFP (red fluorescent protein).

5. The fluorescent indicator protein according to claim 4, wherein the fluorescent indicator protein has an amino acid sequence selected from the group consisting of SEQ ID NO: 33 to 35.

6. A fluorescent indicator protein having an increased sensitivity to the concentration of sugars, which is represented by Formula I:

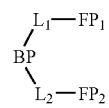

[Formula I]

wherein the BP is a MBP mutant which has at least one of mutations of Asp14Leu, Lys15Phe, Trp62Tyr, and Glu111Tyr in the amino acid sequence set forth in SEQ ID NO: 30; $L_1$ and $L_2$ consist of two amino acids, wherein $L_1$ is Leu-His and $L_2$, is Gly-Ser and wherein $L_1$ is attached to the N-terminal end of BP and $L_2$, is attached to the C-terminal end of BP; $FP_1$ is selected from the group consisting of ECFP (enhanced cyan fluorescent protein), EBFP (enhanced blue fluorescent protein) and EGFP (enhanced green fluorescent protein), and $FP_2$ is selected from the group consisting of EYFP (enhanced yellow fluorescent protein), EGFP (enhanced green fluorescent protein) and RFP (red fluorescent protein).

7. The fluorescent indicator protein according to claim 6, wherein said fluorescent indicator protein has an amino acid sequence set forth in SEQ ID NO: 39.

* * * * *